US011661439B2

(12) United States Patent
Schneider et al.

(10) Patent No.: US 11,661,439 B2
(45) Date of Patent: May 30, 2023

(54) PEPTIDE HYDROGELS AND USE THEREOF

(71) Applicant: The United States of America, as represented by the Secretary, Department of Health and Human Services, Bethesda, MD (US)

(72) Inventors: Joel Schneider, Frederick, MD (US); Scott Walsh, Olney, MD (US); Stephen Miller, Rockville, MD (US); Yuji Yamada, Frederick, MD (US); Scott Durum, Frederick, MD (US); Caroline Andrews, Frederick, MD (US); Wenqing Li, Frederick, MD (US); Julie Hixon, Hagerstown, MD (US); Steven Tau, Manchester, NH (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 273 days.

(21) Appl. No.: 16/954,492

(22) PCT Filed: Dec. 17, 2017

(86) PCT No.: PCT/US2017/066893
§ 371 (c)(1),
(2) Date: Jun. 16, 2020

(87) PCT Pub. No.: WO2019/117976
PCT Pub. Date: Jun. 20, 2019

(65) Prior Publication Data
US 2021/0079042 A1 Mar. 18, 2021

(51) Int. Cl.
| | |
|---|---|
| *C07K 7/08* | (2006.01) |
| *A61K 9/00* | (2006.01) |
| *A61K 9/06* | (2006.01) |
| *A61K 35/17* | (2015.01) |
| *A61L 27/22* | (2006.01) |
| *A61L 27/52* | (2006.01) |
| *A61L 27/54* | (2006.01) |
| *C07K 14/54* | (2006.01) |
| *C07K 14/705* | (2006.01) |
| *C12N 5/00* | (2006.01) |
| *A61K 38/00* | (2006.01) |

(52) U.S. Cl.
CPC .............. *C07K 7/08* (2013.01); *A61K 9/0019* (2013.01); *A61K 9/06* (2013.01); *A61K 35/17* (2013.01); *A61L 27/227* (2013.01); *A61L 27/52* (2013.01); *A61L 27/54* (2013.01); *C07K 14/5418* (2013.01); *C07K 14/705* (2013.01); *C12N 5/0018* (2013.01); *C12N 5/0062* (2013.01); *A61K 38/00* (2013.01); *A61L 2400/06* (2013.01); *C07K 2319/00* (2013.01); *C07K 2319/33* (2013.01); *C07K 2319/35* (2013.01); *C12N 2501/999* (2013.01); *C12N 2513/00* (2013.01)

(58) Field of Classification Search
None
See application file for complete search history.

(56) References Cited

U.S. PATENT DOCUMENTS

| | | | |
|---|---|---|---|
| 6,361,797 B1 | 3/2002 | Kuzma et al. | |
| 7,858,585 B2 | 12/2010 | Ozbas et al. | |
| 7,884,185 B2 | 2/2011 | Schneider et al. | |
| 2009/0238788 A1* | 9/2009 | Butterick ................ | A61L 27/22 424/85.1 |
| 2010/0034881 A1 | 2/2010 | Schneider et al. | |
| 2014/0187487 A1 | 7/2014 | Shoichet et al. | |
| 2014/0302144 A1 | 10/2014 | Koutsopoulos et al. | |
| 2017/0196818 A1* | 7/2017 | Shin ....................... | C12N 11/10 |

FOREIGN PATENT DOCUMENTS

| | | |
|---|---|---|
| WO | WO 2007/059491 A2 | 5/2007 |
| WO | WO 2009/117497 A1 | 9/2009 |
| WO | WO 2010/017369 A2 | 2/2010 |
| WO | WO 2010/151353 A2 | 12/2010 |
| WO | WO 2011/112856 A2 | 9/2011 |
| WO | WO 2012/008967 A1 | 1/2012 |
| WO | WO 2016/118871 A1 | 7/2016 |

OTHER PUBLICATIONS

Miller et al. "Tunable Protein Release from a Peptide Hydrogel" Poster presentation. American Peptide Symposium: New Heights in Peptide Research: 142. (Year: 2017).*
Nagy-Smith et al. "Protein release from highly charged peptide hydrogel networks" J. Materials Chemistry B 4:1999-2007. (Year: 2016).*
Anonymous "Custom Peptide Modifications" GenScript http://www.genscript.com:80/peptide_modification.html (Year: 2015).*
Altunbas et al., "Encapsulation of Curcumin in Self-Assembling Peptide Hydrogels as Injectable Drug Delivery Vehicles," *Biomaterials* 32.25: 5906-5914, Sep. 2011.
Battig et al., "Programmable Release of Multiple Protein Drugs from Aptamer-Functionalized Hydrogels via Nucleic Hybridization," *J Am Chem Soc.* 134: 12410-12413, Jul. 2012.
Branco et al., "The Effect of Protein Structure on their Controlled Release from an Injectable Peptide Hydrogel," *Biomaterials* 31.36: 9527-9534, Dec. 2010.

(Continued)

*Primary Examiner* — Sudhakar Katakam
*Assistant Examiner* — Zachary J Miknis
(74) *Attorney, Agent, or Firm* — Klarquist Sparkman, LLP

(57) ABSTRACT

This disclosure provides novel anionic amphiphilic β-hairpin peptides that self-assemble under appropriate conditions to form a reversible gel-sol hydrogel that can be used, for example, to readily deliver protein therapeutics and cells by injection to a target location in a subject.

32 Claims, 19 Drawing Sheets

Figure 1A:
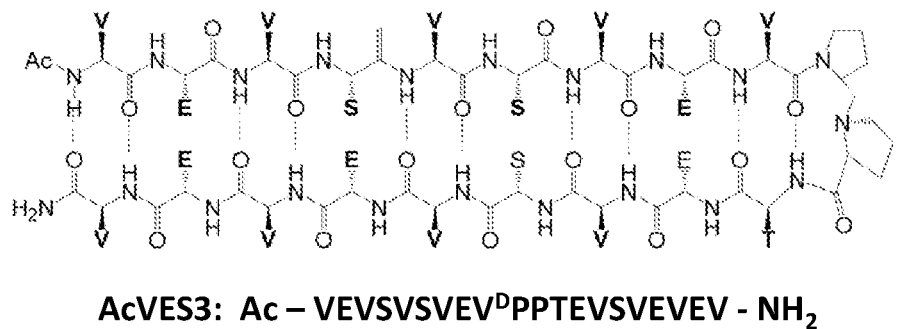

Specification includes a Sequence Listing.

(56) References Cited

OTHER PUBLICATIONS

Habibi et al., "Self-Assembled Peptide-Based Nanostructures: Smart Nanomaterials Toward Targeted Drug Delivery," *Nano Today* 11: 41-60, 2016.
Haines-Butterick et al., "Controlling Hydrogelation Kinetics by Peptide Design for Three-Dimensional Encapsulation and Injectable Delivery of Cells," *Proc Natl Acad Sci USA* 104.19: 7791-7796, May 2007.
Haines-Butterick et al., "In Vitro Assessment of the Pro-Inflammatory Potential of β-hairpin Peptide Hydrogels," *Biomaterials* 29.31: 4164-4169, Nov. 2008.
Hirano et al., "Synthesis and Cell Attachment Activity of Bioactive Oligopeptides: RGD, RGDS, RGDV, and RGDT," *J Biomed Mater Res*. 25.12: 1523-1534, Dec. 1991.
Huie et al., "Correlations Between Structure, Material Properties and Bioproperties in Self-Assembled β-hairpin Peptide Hydrogels," *Faraday Discuss*. 139: 251-420, 2008.
Hunt and Grover, "Cell Encapsulation using Biopolymer Gels for Regenerative Medicine," *Biotechnol Lett*. 32: 733-742, 2010.
International Search Report and Written Opinion Issued in Application No. PCT/US2019/017354, dated May 15, 2019, 15 pages.
Jacob et al., "Self Healing Hydrogels Composed of Amyloid Nano Fibrils for Cell Culture and Stem Cell Differentiation," *Biomaterials* 54: 97-105, 2015.
Kang et al., "Sequence Effects of Self-Assembling MultiDomain Peptide Hydrogels on Encapsulated SHED Cells," *Biomacromolecules* 15: 2004-2011, May 2014.
Kanta, "Collagen Matrix as a Tool in Studying Fibroblastic Cell Behavior," *Cell Adhesion & Migration* 9.4: 308-316, Jul./Aug. 2015.
Koutsopoulos and Zhang, "Two-Layered Injectable Self-Assembling Peptide Scaffold hydrogels for Long-Term Sustained Release of Human Antibodies," *J Contol Release* 160.3: 451-458, Jun. 2012.
Lindsey et al., "Beta Hairpin Peptide Hydrogels as an Injectable Solid Vehicle for Neurotrophic Growth Factor Delivery," *Biomacromolecules* 16: 2672-2683, Jul. 2015.
Majumder et al., "Two-Stage Peptide Hydrogels as Sprayable miRNA Depot for Malignant Pleural Mesothelioma," Poster Session I, National Institutes of Health Research Festival, Sep. 13, 2017. Abstract.
Martino et al., "Heparin-Binding Domain of Fibrin(ogen) Binds Growth Factors and Promotes Tissue Repair when Incorporated within a Synthetic Matrix," *Proc Natl Acad Sci USA* 110.12: 4563-4568, Mar. 2013.
Miller et al., "YI-P145 Tunable Protein Release from a Peptide Hydrogel," Poster at American Peptide Symposium: New Heights in Peptide Research: 142, Jun. 2017. Abstract.
Nagai et al., "The Mechanical Stimulation of Cells in 3D Culture within a Self-Assembling Peptide Hydrogel," *Biomaterials* 33: 1044-1051, 2012.

Nagy-Smith et al., "Protein Release from Highly Charged Peptide Hydrogel Networks," *J Mat Chem B*. 4: 1999-2007, 2016.
Oikonomopoulos et al., "Optimization of Human Mesenchymal Stem Cell Manufacturing: The Effects of Animal/Xeno-Free Media," *Sci Rep*. 5: 16570, Nov. 2015.
Segovia et al., "Hydrogel Doped with Nanoparticles for Local Sustained Release of siRNA in Breast Cancer," *Adv Healthcare Mater*. 4: 271-280, 2015.
Shukla et al., "Peptides Used in the Delivery of Small Noncoding RNA," *Mol Pharmaceutics* 11: 3395-3408, Aug. 2014.
Sinthuvanich et al., "Iterative Design of Peptide-Based Hydrogels and the Effect of Network Electrostatics on Primary Chondrocyte Behavior," *Biomaterials* 33.30: 7478-7488, Oct. 2012.
Tam et al., "Transparent Porous Polysaccharide Cryogels Provide Biochemically Defined Matrices for Tunable 3D Cell Culture," *Chem Mater*. 28: 3762-3770, Apr. 2016.
Terpe, "Overview of Tag Protein Fusions: From Molecular and Biochemical Fundamentals to Commercial Systems," *Appl Microbiol Biotechnol*. 60: 523-533, 2003.
Vaishya et al., "Long-Term Delivery of Protein Therapeutics," *Expert Opin Drug Deliv*. 12.3: 415-440, Mar. 2015.
Vulic and Shoichet, "Affinity-Based Drug Delivery Systems for Tissue Repair and Regeneration," *Biomacromolecules* 15: 3867-3880, Sep. 2014.
Vulic and Shoichet, "Tunable Growth Factor Delivery from Injectable Hydrogels for Tissue Engineering," *J Am Chem Soc*. 134: 882-885, 2012.
Wang and Burdick, "Engineered Hydrogels for Local and Sustained Delivery of RNA-Interference Therapies," *Adv Healthcare Mater* 6: 1601041, 2017.
Wieduwild et al., "A Repertoire of Peptide Tags for Controlled Drug Release from Injectable Noncovalent Hydrogel," *Biomacromolecules* 15: 2058-2066, May 2014.
Worthington et al., "Peptide Hydrogels—Versatile Matrices for 3D Cell Culture in Cancer Medicine," *Frontiers in Oncology* 5.92: 1-10, Apr. 2015.
Yamada et al., "Macromolecule-Network Electrostatics Controlling Delivery of the Biotherapeutic Cell Modulator TIMP-2," *Biomacromolecules* 19: 1285-1293, Mar. 2018.
Yamada et al., "YI-P252 Design of Self-Assembling Peptide Gies for 3D Cell Culture and Cell Delivery," Poster at the 25th American Peptide Symposium: New Heights in Peptide Research: 142, Jun. 2017. Abstract.
Yan et al., "Injectable Solid Hydrogel: Mechanism of Shear-Thinning and Immediate Recovery of Injectable β-hairpin Peptide Hydrogels," *Soft Matter* 6.20: 5143-5156, Oct. 2010.
Yan et al., "Injectable Solid Peptide Hydrogel as Cell Carrier: Effects of Shear Flow on Hydrogel and Cell Payload," *Langmuir* 28.14: 6076-6087, Apr. 2012.
Zamuner et al., "Design of Decorated Self-Assembling Peptide Hydrogels as Architecture for Mesenchymal Stem Cells," *Materials* 9.727: 1-18, 2016.

\* cited by examiner

AcVES3: Ac – VEVSVSVEV$^D$PPTEVSVEVEV - NH$_2$

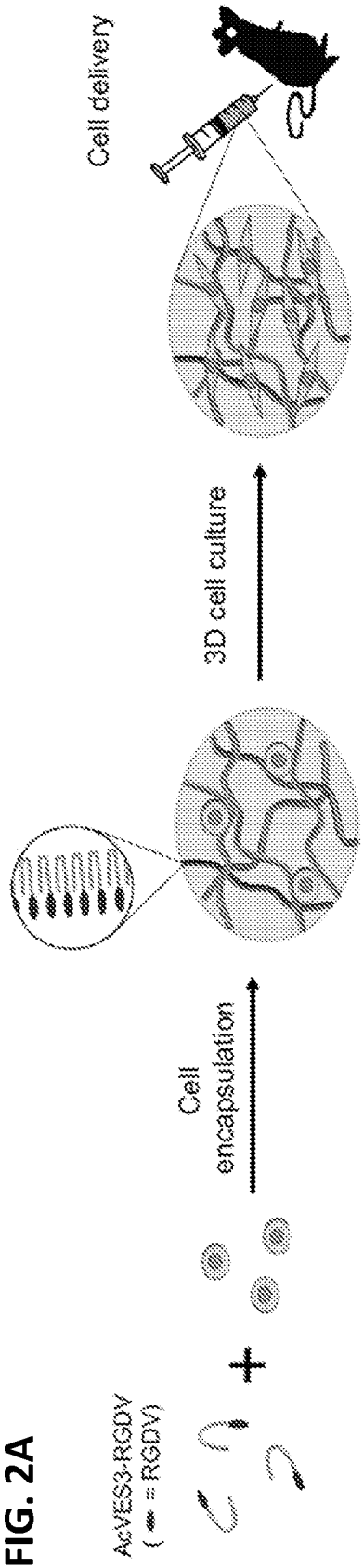

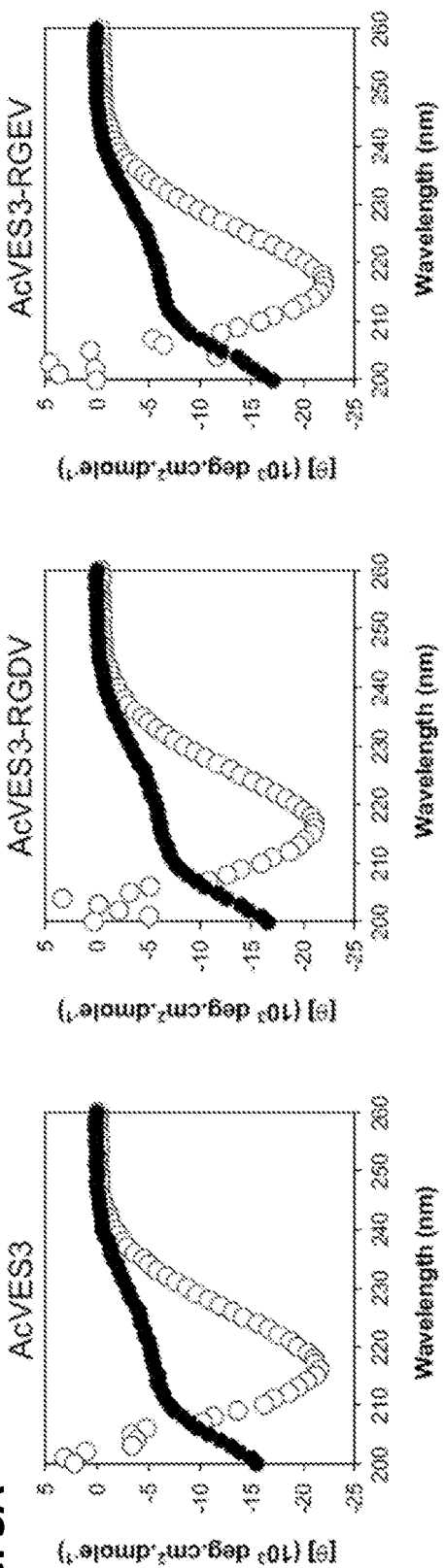
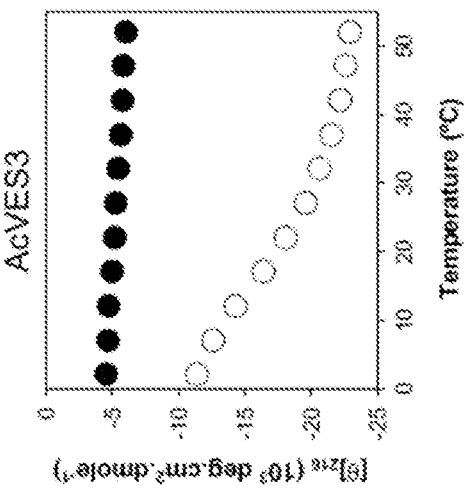
FIG. 3A
FIG. 3B

FIG. 6A
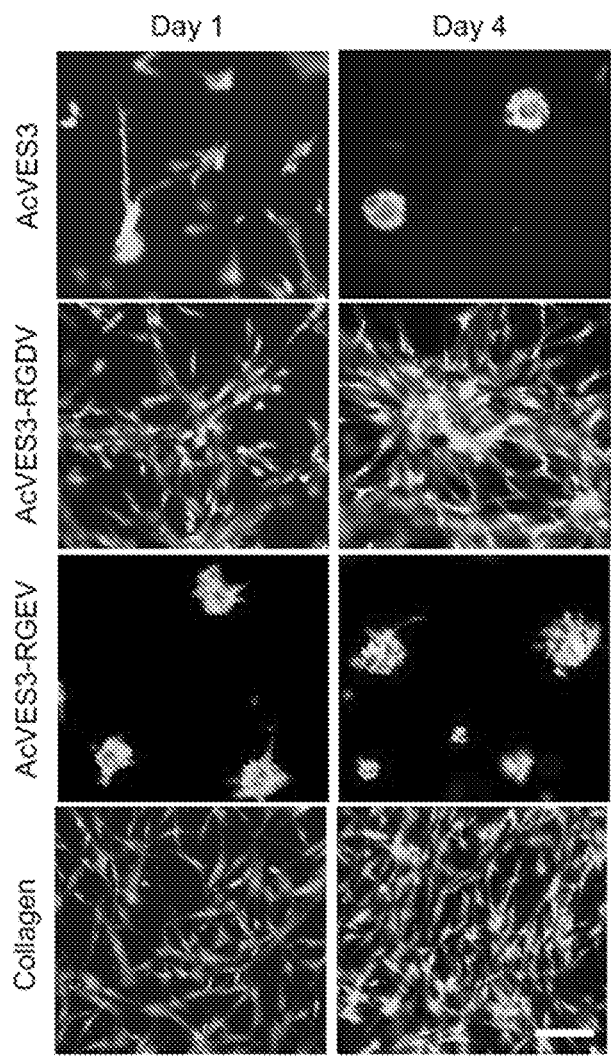
FIG. 6B
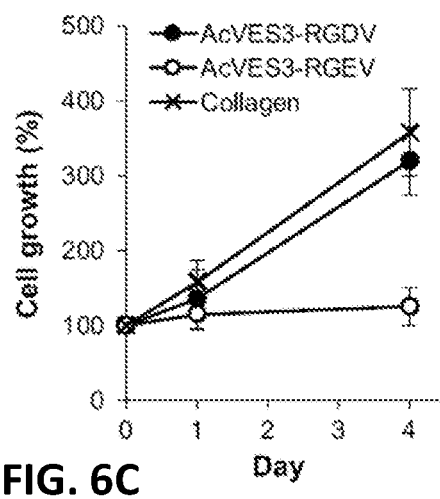
FIG. 6C
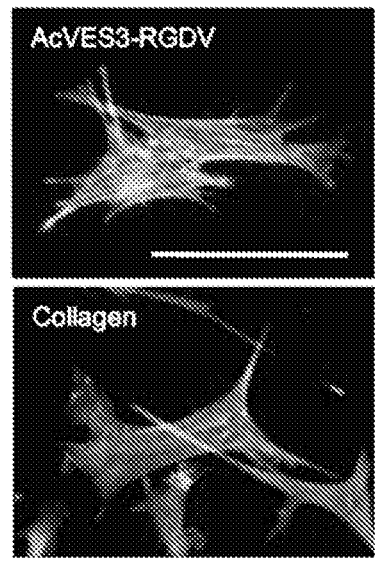
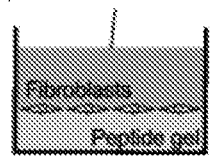

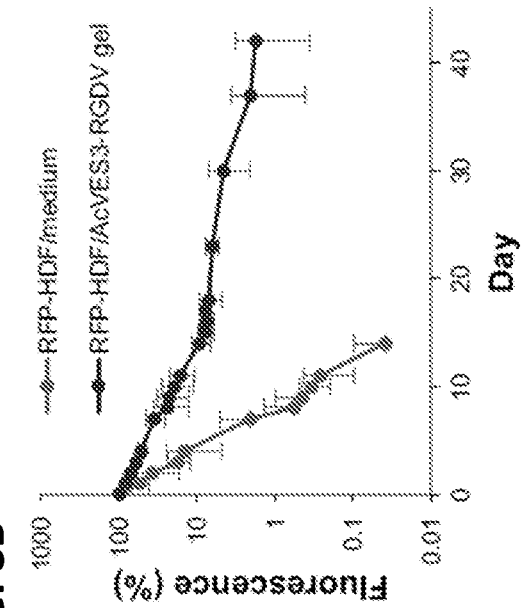
FIG. 8B
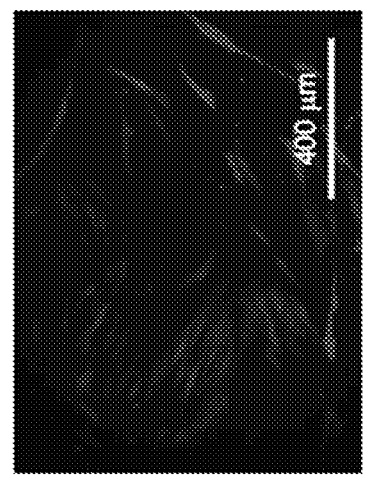
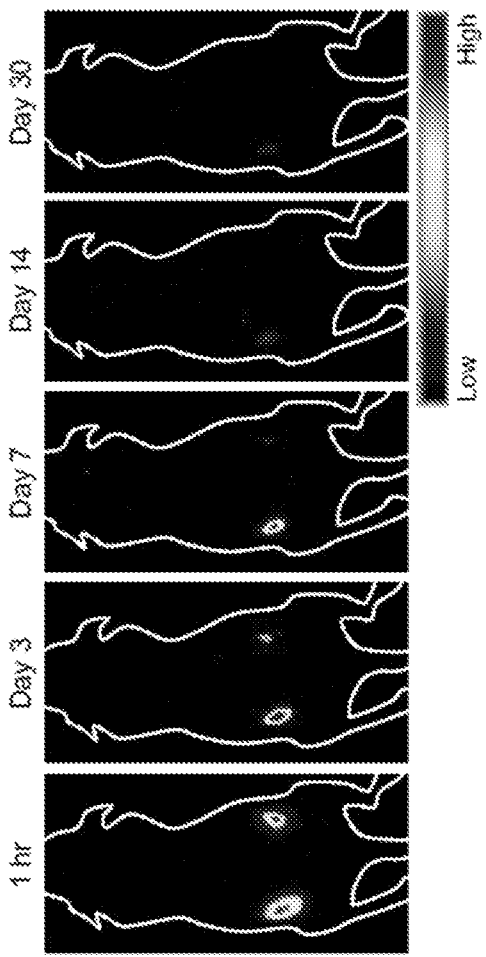
FIG. 8A
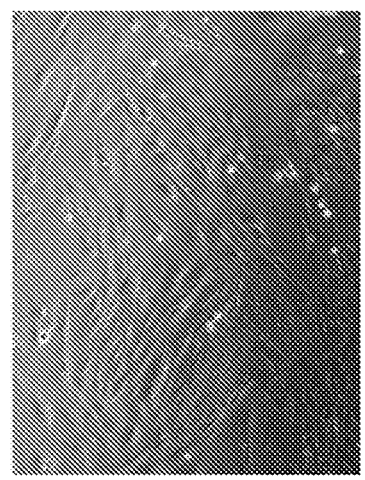
FIG. 8D
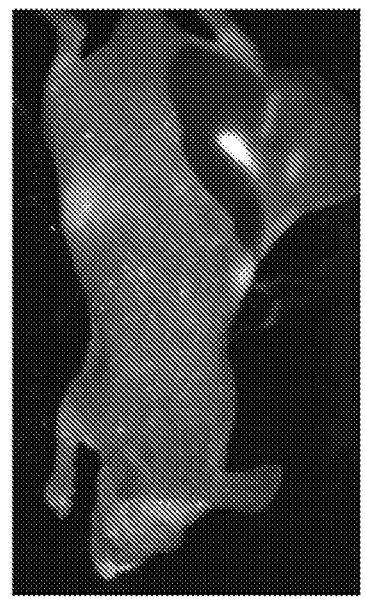
FIG. 8C Encapsulated protein does not alter sheer-thinning of AcVES3 peptide hydrogels

Dual, staggered release of similarly charged proteins

*In vitro* release of mRuby3 and RH5-mRuby3 from AcVES3 Hydrogel

SEQUENCE LISTING

```
<160> NUMBER OF SEQ ID NOS: 19

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(1)
<223> OTHER INFORMATION: Xaa is independently selected from any one of
      L, I, T, and V
<220> FEATURE:
<221> NAME/KEY: misc_feature
<222> LOCATION: (2)..(2)
<223> OTHER INFORMATION: Xaa is independently selected from any one of
      D, E, and S
<220> FEATURE:
<221> NAME/KEY: misc_feature
<222> LOCATION: (3)..(3)
<223> OTHER INFORMATION: Xaa is independently selected from any one of
      L, I, T, and V
<220> FEATURE:
<221> NAME/KEY: misc_feature
<222> LOCATION: (4)..(4)
<223> OTHER INFORMATION: Xaa is independently selected from any one of
      D, E, Q, N, T, K, R, and S
<220> FEATURE:
<221> NAME/KEY: misc_feature
<222> LOCATION: (5)..(5)
```

```
<223> OTHER INFORMATION: Xaa is independently selected from any one of
      L, I, T, and V
<220> FEATURE:
<221> NAME/KEY: misc_feature
<222> LOCATION: (6)..(6)
<223> OTHER INFORMATION: Xaa is independently selected from any one of
      D, E, Q, N, T, K, R, and S
<220> FEATURE:
<221> NAME/KEY: misc_feature
<222> LOCATION: (7)..(7)
<223> OTHER INFORMATION: Xaa is independently selected from any one of
      L, I, T, and V
<220> FEATURE:
<221> NAME/KEY: misc_feature
<222> LOCATION: (8)..(8)
<223> OTHER INFORMATION: Xaa is independently selected from any one of
      D, E, and S
<220> FEATURE:
<221> NAME/KEY: misc_feature
<222> LOCATION: (9)..(9)
<223> OTHER INFORMATION: Xaa is independently selected from any one of
      L, I, T, and V
<220> FEATURE:
<221> NAME/KEY: misc_feature
<222> LOCATION: (12)..(12)
<223> OTHER INFORMATION: Xaa is independently selected from any one of
      L, I, T, and V
<220> FEATURE:
<221> NAME/KEY: misc_feature
<222> LOCATION: (13)..(13)
<223> OTHER INFORMATION: Xaa is independently selected from any one of
      D, E, and S
<220> FEATURE:
<221> NAME/KEY: misc_feature
<222> LOCATION: (14)..(14)
<223> OTHER INFORMATION: Xaa is independently selected from any one of
      L, I, T, and V
<220> FEATURE:
<221> NAME/KEY: misc_feature
<222> LOCATION: (15)..(15)
<223> OTHER INFORMATION: Xaa is independently selected from any one of
      D, E, Q, N, T, K, R, and S
<220> FEATURE:
<221> NAME/KEY: misc_feature
<222> LOCATION: (16)..(16)
<223> OTHER INFORMATION: Xaa is independently selected from any one of
      L, I, T, and V
<220> FEATURE:
<221> NAME/KEY: misc_feature
<222> LOCATION: (17)..(17)
<223> OTHER INFORMATION: Xaa is independently selected from any one of
      D, E, and S
<220> FEATURE:
<221> NAME/KEY: misc_feature
<222> LOCATION: (18)..(18)
<223> OTHER INFORMATION: Xaa is independently selected from any one of
      L, I, T, and V
<220> FEATURE:
<221> NAME/KEY: misc_feature
<222> LOCATION: (19)..(19)
<223> OTHER INFORMATION: Xaa is independently selected from any one of
      D, E, and S
<220> FEATURE:
<221> NAME/KEY: misc_feature
<222> LOCATION: (20)..(20)
<223> OTHER INFORMATION: Xaa is independently selected from any one of
      L, I, T, and V

<400> SEQUENCE: 1

Xaa Xaa Xaa Xaa Xaa Xaa Xaa Xaa Xaa Asn Gly Xaa Xaa Xaa Xaa Xaa
1               5                   10                  15

Xaa Xaa Xaa Xaa
            20

<210> SEQ ID NO 2
<211> LENGTH: 20
```

```
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(1)
<223> OTHER INFORMATION: Xaa is independently selected from any one of
      L, I, T, and V
<220> FEATURE:
<221> NAME/KEY: misc_feature
<222> LOCATION: (2)..(2)
<223> OTHER INFORMATION: Xaa is independently selected from any one of
      D, E, and S
<220> FEATURE:
<221> NAME/KEY: misc_feature
<222> LOCATION: (3)..(3)
<223> OTHER INFORMATION: Xaa is independently selected from any one of
      L, I, T, and V
<220> FEATURE:
<221> NAME/KEY: misc_feature
<222> LOCATION: (5)..(5)
<223> OTHER INFORMATION: Xaa is independently selected from any one of
      L, I, T, and V
<220> FEATURE:
<221> NAME/KEY: misc_feature
<222> LOCATION: (7)..(7)
<223> OTHER INFORMATION: Xaa is independently selected from any one of
      L, I, T, and V
<220> FEATURE:
<221> NAME/KEY: misc_feature
<222> LOCATION: (8)..(8)
<223> OTHER INFORMATION: Xaa is independently selected from any one of
      D, E, and S
<220> FEATURE:
<221> NAME/KEY: misc_feature
<222> LOCATION: (9)..(9)
<223> OTHER INFORMATION: Xaa is independently selected from any one of
      L, I, T, and V
<220> FEATURE:
<221> NAME/KEY: misc_feature
<222> LOCATION: (12)..(12)
<223> OTHER INFORMATION: Xaa is independently selected from any one of
      L, I, T, and V
<220> FEATURE:
<221> NAME/KEY: misc_feature
<222> LOCATION: (13)..(13)
<223> OTHER INFORMATION: Xaa is independently selected from any one of
      D, E, and S
<220> FEATURE:
<221> NAME/KEY: misc_feature
<222> LOCATION: (14)..(14)
<223> OTHER INFORMATION: Xaa is independently selected from any one of
      L, I, T, and V
<220> FEATURE:
<221> NAME/KEY: misc_feature
<222> LOCATION: (16)..(16)
<223> OTHER INFORMATION: Xaa is independently selected from any one of
      L, I, T, and V
<220> FEATURE:
<221> NAME/KEY: misc_feature
<222> LOCATION: (17)..(17)
<223> OTHER INFORMATION: Xaa is independently selected from any one of
      D, E, and S
<220> FEATURE:
<221> NAME/KEY: misc_feature
<222> LOCATION: (18)..(18)
<223> OTHER INFORMATION: Xaa is independently selected from any one of
      L, I, T, and V
<220> FEATURE:
<221> NAME/KEY: misc_feature
<222> LOCATION: (19)..(19)
<223> OTHER INFORMATION: Xaa is independently selected from any one of
      D, E, and S
<220> FEATURE:
<221> NAME/KEY: misc_feature
<222> LOCATION: (20)..(20)
<223> OTHER INFORMATION: Xaa is independently selected from any one of
      L, I, T, and V
```

<400> SEQUENCE: 2

Xaa Xaa Xaa Ser Xaa Ser Xaa Xaa Xaa Asn Gly Xaa Xaa Xaa Ser Xaa
1               5                   10                  15

Xaa Xaa Xaa Xaa
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide sequence
<220> FEATURE:
<221> NAME/KEY: misc_feature
<222> LOCATION: (1)..(1)
<223> OTHER INFORMATION: Xaa is independently selected from any one of
      L, I, T, and V
<220> FEATURE:
<221> NAME/KEY: misc_feature
<222> LOCATION: (3)..(3)
<223> OTHER INFORMATION: Xaa is independently selected from any one of
      L, I, T, and V
<220> FEATURE:
<221> NAME/KEY: misc_feature
<222> LOCATION: (5)..(5)
<223> OTHER INFORMATION: Xaa is independently selected from any one of
      L, I, T, and V
<220> FEATURE:
<221> NAME/KEY: misc_feature
<222> LOCATION: (7)..(7)
<223> OTHER INFORMATION: Xaa is independently selected from any one of
      L, I, T, and V
<220> FEATURE:
<221> NAME/KEY: misc_feature
<222> LOCATION: (9)..(9)
<223> OTHER INFORMATION: Xaa is independently selected from any one of
      L, I, T, and V
<220> FEATURE:
<221> NAME/KEY: misc_feature
<222> LOCATION: (12)..(12)
<223> OTHER INFORMATION: Xaa is independently selected from any one of
      L, I, T, and V
<220> FEATURE:
<221> NAME/KEY: misc_feature
<222> LOCATION: (14)..(14)
<223> OTHER INFORMATION: Xaa is independently selected from any one of
      L, I, T, and V
<220> FEATURE:
<221> NAME/KEY: misc_feature
<222> LOCATION: (16)..(16)
<223> OTHER INFORMATION: Xaa is independently selected from any one of
      L, I, T, and V
<220> FEATURE:
<221> NAME/KEY: misc_feature
<222> LOCATION: (18)..(18)
<223> OTHER INFORMATION: Xaa is independently selected from any one of
      L, I, T, and V
<220> FEATURE:
<221> NAME/KEY: misc_feature
<222> LOCATION: (20)..(20)
<223> OTHER INFORMATION: Xaa is independently selected from any one of
      L, I, T, and V

<400> SEQUENCE: 3

Xaa Glu Xaa Ser Xaa Ser Xaa Glu Xaa Asn Gly Xaa Glu Xaa Ser Xaa
1               5                   10                  15

Glu Xaa Glu Xaa
            20

<210> SEQ ID NO 4
<211> LENGTH: 20
<212> TYPE: PRT

```
<213> ORGANISM: Artificial Sequence
<220> FEATURE:
<223> OTHER INFORMATION: Synthetic peptide sequence

<400> SEQUENCE: 4

Val Glu Val Ser Val Ser Val Glu Val Asn Gly Thr Glu Val Ser Val
1               5                   10                  15

Glu Val Glu Val
            20

<210> SEQ ID NO 5
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 5

Arg Gly Asp Val
1

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 6

Lys Gln Ala Gly Asp Val
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 7

Lys Arg Leu Asp Gly Ser
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic peptide sequence

<400> SEQUENCE: 8

Tyr Tyr Asp Leu Arg
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 9

Phe Tyr Phe Asp Leu Arg
1               5

<210> SEQ ID NO 10
```

```
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 10

Gly Gly Gly Gly
1

<210> SEQ ID NO 11
<211> LENGTH: 177
<212> TYPE: PRT
<213> ORGANISM: homo sapiens

<400> SEQUENCE: 11

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30

Asp Gly Lys Gln Tyr Glu Ser Val Leu Met Val Ser Ile Asp Gln Leu
        35                  40                  45

Leu Asp Ser Met Lys Glu Ile Gly Ser Asn Cys Leu Asn Asn Glu Phe
    50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
        115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 12
<211> LENGTH: 4
<212> TYPE: PRT
<213> ORGANISM: Artificial Sequence
<220> FEATURE:
<223> OTHER INFORMATION: Synthetic peptide sequence

<400> SEQUENCE: 12

Gly Arg His Arg
1

<210> SEQ ID NO 13
<211> LENGTH: 6
<212> TYPE: PRT
<213> ORGANISM: Artificial Sequence
<220> FEATURE:
<223> OTHER INFORMATION: Synthetic peptide sequence

<400> SEQUENCE: 13

Gly Arg His Arg His Arg
1               5
```

```
<210> SEQ ID NO 14
<211> LENGTH: 8
<212> TYPE: PRT
<213> ORGANISM: Artificial Sequence
<220> FEATURE:
<223> OTHER INFORMATION: Synthetic peptide sequence

<400> SEQUENCE: 14

Gly Arg His Arg His Arg His Arg
1               5

<210> SEQ ID NO 15
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 15

Gly Arg His Arg His Arg His Arg His Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide sequence

<400> SEQUENCE: 16

Gly Arg His Arg His Arg His Arg His Arg His Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic peptide sequence

<400> SEQUENCE: 17

Gly Arg His Arg His Arg His Arg His Arg His Arg His Arg
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic peptide sequence

<400> SEQUENCE: 18

Gly Gly Ser Gly Ser Gly Gly Ser Gly Ser
1               5                   10

<210> SEQ ID NO 19
<211> LENGTH: 239
<212> TYPE: PRT
<213> ORGANISM: Artificial Sequence
<220> FEATURE:
<223> OTHER INFORMATION: Engineered Green Fluorescent Protein

<400> SEQUENCE: 19

Met Val Ser Lys Gly Glu Glu Leu Phe Thr Gly Val Val Pro Ile Leu
1               5                   10                  15
```

```
Val Glu Leu Asp Gly Asp Val Asn Gly His Lys Phe Ser Val Ser Gly
             20              25              30
Glu Gly Glu Gly Asp Ala Thr Tyr Gly Lys Leu Thr Leu Lys Phe Ile
         35              40              45
Cys Thr Thr Gly Lys Leu Pro Val Pro Trp Pro Thr Leu Val Thr Thr
     50              55              60
Leu Thr Tyr Gly Val Gln Cys Phe Ser Arg Tyr Pro Asp His Met Lys
 65              70              75              80
Gln His Asp Phe Phe Lys Ser Ala Met Pro Glu Gly Tyr Val Gln Glu
             85              90              95
Arg Thr Ile Phe Phe Lys Asp Asp Gly Asn Tyr Lys Thr Arg Ala Glu
         100             105             110
Val Lys Phe Glu Gly Asp Thr Leu Val Asn Arg Ile Glu Leu Lys Gly
         115             120             125
Ile Asp Phe Lys Glu Asp Gly Asn Ile Leu Gly His Lys Leu Glu Tyr
 130             135             140
Asn Tyr Asn Ser His Asn Val Tyr Ile Met Ala Asp Lys Gln Lys Asn
145             150             155             160
Gly Ile Lys Val Asn Phe Lys Ile Arg His Asn Ile Glu Asp Gly Ser
             165             170             175
Val Gln Leu Ala Asp His Tyr Gln Gln Asn Thr Pro Ile Gly Asp Gly
         180             185             190
Pro Val Leu Leu Pro Asp Asn His Tyr Leu Ser Thr Gln Ser Ala Leu
         195             200             205
Ser Lys Asp Pro Asn Glu Lys Arg Asp His Met Val Leu Leu Glu Phe
210             215             220
Val Thr Ala Ala Gly Ile Thr Leu Gly Met Asp Glu Leu Tyr Lys
225             230             235
```

PEPTIDE HYDROGELS AND USE THEREOF

CROSS REFERENCE TO RELATED APPLICATIONS

This is the U.S. National Stage of International Application No. PCT/US2017/066893, filed Dec. 17, 2017, which was published in English under PCT Article 21(2), and is incorporated herein in its entirety.

FIELD OF THE DISCLOSURE

This relates to anionic peptides and peptide hydrogels that can undergo multiple gel-to-solution (gel-sol) and solution-to-gel (sol-gel) phase transitions, and their use, such as for controlled delivery of proteins and cells to a subject, and for culturing mammalian cells.

BACKGROUND

The use of injectable hydrogels allows the local delivery of encapsulated protein therapeutics directly to tissue, limiting systemic distribution of the protein therapeutic and any associated toxicity. However, current strategies for hydrogel mediated protein delivery still have challenges that must be overcome before becoming clinically viable Limitations include engineering hydrogels that have minimal biocompatibility complications and will predictably control the rate of protein release to neighboring tissue over a desired period of time for optimal therapeutic outcome. Currently, hydrogel characteristics (mesh size, etc.) are relied upon to control the release profile of the encapsulated protein. Thus, for every distinct protein therapeutic, a corresponding hydrogel must be engineered (one protein-one gel); this represents a tremendous research and regulatory burden.

Several attempts have been made to use synthetic hydrogels for cell encapsulation and 3D culturing. However, the adhesion and proliferation of encapsulated cells in injectable hydrogels was not possible, limiting the utility of such systems for delivery of cell-based therapeutics.

SUMMARY

This disclose provides novel anionic amphiphilic β-hairpin peptides that self-assemble under appropriate conditions to form a reversible gel-sol hydrogel that can be used to readily deliver protein therapeutics and cells by injection to a target location in a subject. Unlike prior peptide hydrogels, the disclosed embodiments are shown to provide tunable protein release in vivo, and further to provide 3D cell culture matrices that avoid the use of non-human media components, promote growth and proliferation of cells in vitro, and continue to encapsulate the cells to retain them in the target location following injection into a target location in a subject.

In some embodiments, an isolated peptide is provided, comprising or consisting of an amino acid sequence set forth as: XBXZXZXBX-[$^D$PP, $^D$PG, or NG]-XBXZXBXBX, wherein each X is independently selected from any one of L, I, T, and V; each B is independently selected from any one of D, E, and S; each Z is independently selected from any one of D, E, Q, N, T, K, R, and S; the $^D$P is a proline that is a D amino acid; the C-terminus of the peptide is amidated or free carboxylic acid; the N-terminus of the peptide is acetylated or free amine; and the peptide is no more than 50 amino acids in length. In several such embodiments, the C-terminus of the peptide is amidated and the N-terminus of the peptide is acetylated. In a non-limiting example, the peptide is the AcVES3 peptide:

$$\text{Ac-VEVSVSVEV}^D\text{PPTEVSVEVEV-NH}_2.$$

The disclosed peptides form an amphiphilic β-hairpin conformation in an aqueous solution comprising 150 mM NaCl and a pH of 7.4 at 25-37° C., and can be used to produce a peptide hydrogel. For example, an aqueous solution containing 2% w/v of a disclosed peptide and 150 mM NaCl and a pH of 7.4 forms a peptide hydrogel comprising a fibrillar network of a plurality of the peptide when incubated at 25-37° C. in a container. The peptide hydrogel undergoes a gel-sol phase transition upon application of shear stress, and a sol-gel phase transition upon removal of the shear stress.

In additional embodiments, a peptide hydrogel formed with a disclosed isolated peptide is provided, such as a peptide hydrogel formed with the AcVES3 peptide. In some embodiments, the peptide hydrogel further comprises a heterologous protein (such as IL-7) dispersed within the peptide hydrogel. In additional embodiments, the peptide hydrogel further comprises a heterologous protein dispersed within the peptide hydrogel, wherein the heterologous protein is fused to a peptide tag having a net positive charge that increases retention of the heterologous protein in the hydrogel.

In some embodiments, an isolated peptide is provided, comprising or consisting of an amino acid sequence set forth as: XBXZXZXBX-[$^D$PP, $^D$PG, or NG]-XBXZXBXBX, wherein each X is independently selected from any one of L, I, T, and V; each B is independently selected from any one of D, E, and S; each Z is independently selected from any one of D, E, Q, N, T, K, R, and S; the $^D$P is a proline that is a D amino acid; the C-terminus of the peptide is amidated or free carboxylic acid; the N-terminus of the peptide is acetylated or free amine; and the peptide is no more than 50 amino acids in length, and the peptide further comprises an amino acid sequence of an integrin binding peptide. In several such embodiments, the C-terminus of the peptide is amidated and the N-terminus of the peptide is acetylated. In a non-limiting example, the peptide is the AcVES3-RGDV peptide:

$$\text{Ac-VEVSVSVEV}^D\text{PPTEVSVEVEVGGGRGDV-NH}_2.$$

The disclosed peptides comprising the amino acid sequence of the integrin binding peptide form an amphiphilic β-hairpin conformation in an aqueous solution comprising 150 mM NaCl and a pH of 7.4 at 25-37° C., and can be used to produce a peptide hydrogel. For example, an aqueous solution containing 2% w/v of a disclosed peptide comprising the amino acid sequence of the integrin binding peptide and 150 mM NaCl and a pH of 7.4 forms a peptide hydrogel comprising a fibrillar network of a plurality of the peptide comprising the amino acid sequence of the integrin binding peptide when incubated at 25-37° C. in a container. The peptide hydrogel undergoes a gel-sol phase transition upon application of shear stress, and a sol-gel phase transition upon removal of the shear stress.

In some embodiments, a peptide hydrogel formed with a disclosed isolated peptide comprising the amino acid sequence of the integrin binding peptide is provided, such as a peptide hydrogel formed with the AcVES3-RGDV peptide. In some embodiments, the peptide hydrogel further comprises mammalian cells (such as CAR T cells) dispersed within the peptide hydrogel, wherein the mammalian cells comprise a cell surface comprising one or more integrin proteins that bind to the integrin binding peptide.

The disclosed peptide hydrogels are cytocompatibile and biocompatible, and can be used in methods of administering mammalian cells (such as CAR T cells) or a heterologous protein (such as IL-7) to a subject, for example, by injecting the hydrogel comprising the heterologous protein or mammalian cells to a target location in the subject.

In some embodiments, a syringe containing a disclosed peptide hydrogel is provided.

Figure 12A:
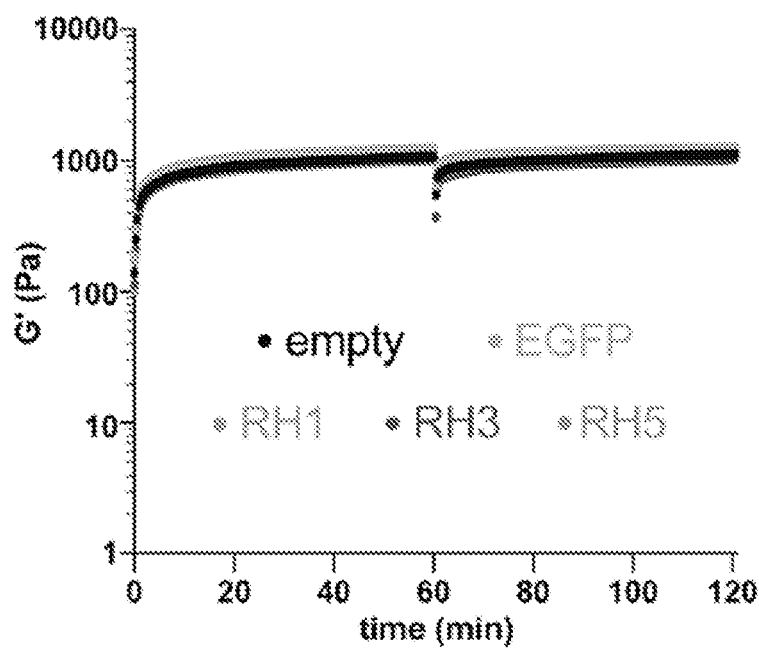
Figure 12B:
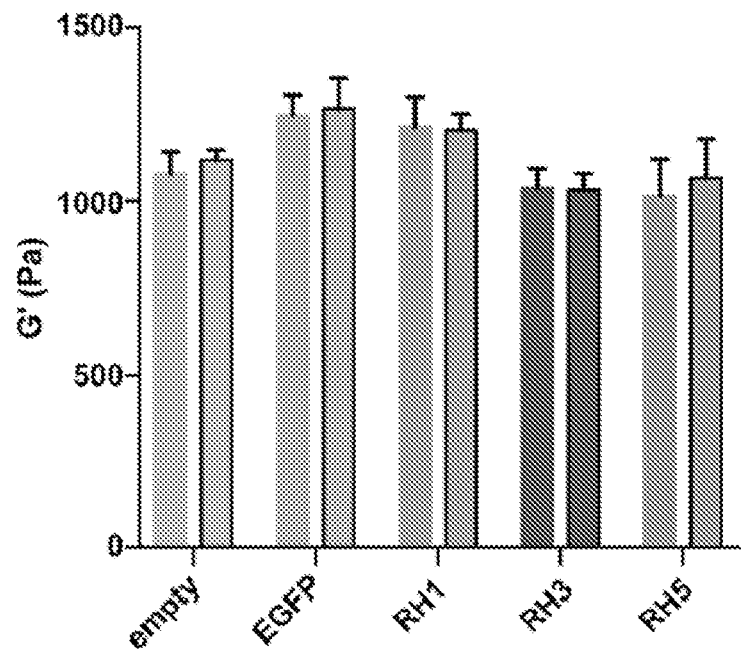

Further provided is a method of culturing mammalian cells in a three-dimensional matrix, comprising, mixing a disclosed peptide comprising the amino acid sequence of the integrin binding peptide and mammalian cells under conditions sufficient to form a peptide hydrogel encapsulating the mammalian cells, wherein the mammalian cells comprise a cell surface comprising one or more integrin proteins that bind to the integrin binding peptide fused to the AcVES3 peptide, and incubating the mammalian cells under conditions sufficient for cell growth and proliferation.

The foregoing and other features and advantages of this disclosure will become more apparent from the following detailed description of several embodiments which proceeds with reference to the accompanying figures.

BRIEF DESCRIPTION OF THE FIGURES

FIGS. 1A and 1B. Illustration of the AcVES3 peptide and corresponding hydrogel. (1A) Structure of AcVES3 peptide in a β-hairpin conformation. (1B) Energy minimized model showing the facial association of AcVES3 β-hairpins within the hydrophobic interface of the fibril bilayer. Two peptides stack on top of each other, with the hydrophobic face of the first peptide forming hydrophobic (van der Waals) interactions to the hydrophobic face of the second peptide. The lateral sides of the peptides form intermolecular interactions with adjacent peptides as the fibril network expands.

FIGS. 2A and 2B. Diagram and composition of β-hairpin peptide hydrogels. (2A) Schematic illustration of cell encapsulation, 3D cell culture, and cell delivery using the AcVES3-RGDV peptide hydrogel. (2B) Sequences and net charges of the peptides.

FIGS. 3A and 3B. Secondary structural characterization of β-hairpin peptide hydrogels. (3A) CD wavelength spectra of peptides in HEPES buffer (O) (25 mM HEPES, 150 mM NaCl, pH 7.4) or water (•) at 37° C. (3B) Temperature-dependent formation of β-sheet structure monitored at $[\theta]_{216}$ (pH 7.4) using CD spectroscopy.

FIG. 4. Fibril visualization of β-hairpin peptide hydrogels. Transmission Electron Microscopy (TEM) images of peptide fibrils and frequency distributions determined from 30 independent measurements (scale bar=100 nm).

FIGS. 5A-5F. Mechanical properties and optical transmittance of β-hairpin peptide hydrogels. (5A-5D) Oscillatory rheological dynamic time sweeps and shear-thin recovery were measured with 0.5 weight percent (wt %) peptide hydrogels and a 0.3 wt % collagen gel by monitoring the storage (solid symbols) and loss (open symbols) moduli. (5A) AcVES3 in HEPES buffer (25 mM HEPES, 150 mM NaCl, pH 7.4). (5B) AcVES3-RGDV in HEPES buffer (circles) or cell culture medium (triangles, 0.5×HEPES-supplemented DMEM 143 mM sucrose). (5C) AcVES3-RGEV in HEPES buffer (circles) or cell culture medium (triangles). (5D) Type I collagen in PBS buffer. The first 60 min displays the onset of gelation under a strain of 0.2% and a frequency of 6 rad $s^{-1}$. Subsequently, the gels were shear-thinned at 1000% strain for 30 s (indicated by dashed line) and allowed to recover by reducing the strain to 0.2%. (5E) Image of a 0.5 wt % AcVES3 hydrogel and a 0.3 wt % collagen hydrogel. (5F) Transmittance measurements of 0.5 wt % peptide hydrogels and a 0.3 wt % collagen hydrogel.

FIGS. 6A-6C. Two-dimensional culturing of human dermal fibroblasts (HDFs). HDFs were cultured on surfaces of 0.5 wt % peptide hydrogels or 0.3 wt % collagen hydrogels in Essential 8 Medium for 4 days. (6A) Live and dead cells were visualized using calcein AM and ethidium homodimer-1 staining (scale bar=100 μm), respectively. (6B) Cell growth was monitored by quantifying cell viability on days 0, 1, and 4. Data are represented as mean±SD of three independent replicates. (6C) Cytoskeleton organization and focal adhesions were stained on day 1 against actin, vinculin, and nuclei (scale bar=100 μm).

FIGS. 7A-7E. Three-dimensional culturing of HDFs. HDFs were 3D cultured with 0.5 wt % peptide hydrogels or 0.3 wt % collagen hydrogels with Essential 8 Medium. (7A) Live and dead cells were visualized on days 1, 4, and 7, using calcein AM and ethidium homodimer-1 staining, respectively (scale bar=100 μm). (7B) Cell growth was monitored by quantifying cell viability on days 1, 4, and 7. Data are represented as mean±SD of three independent replicates. (7C) A pseudo-colored composite of varying depths (0-500 μm) of Z-stacked images of live cells stained with calcein AM in 0.5% AcVES3-RGDV hydrogels on day 4 (scale bar=100 μm). Cells were observed at all measured depths of the hydrogel. (7D) Z-stack image of cytoskeleton organization in the hydrogels on day 4 with actin and nuclei (scale bar=100 μm) stained. (7E) Shear-thinned recovery of cells encapsulated in 0.5 wt % AcVES3-RGDV hydrogel after 3D culturing for 4 days. Hydrogels were shear-thinned at 1000% strain for 30 s (indicated by dashed line) every 10 min and allowed to recover by reducing the strain to 0.2%.

FIGS. 8A-8D. Hydrogel-based delivery of HDF cells in vivo. (8A) Red fluorescent protein-expressing human dermal fibroblasts (RFP-HDFs) were encapsulated in AcVES3-RGDV hydrogels ($10^6$ cells per 100 μL) and injected into the left dorsal region. For a negative control, further cells were suspended in medium ($10^6$ cells per 100 μL) and injected into the right dorsal region of the same mouse. RFP fluorescent images were recorded over 30 days. (8B) RFP fluorescence from a region of interest plotted as a function of time. (8C) RFP fluorescence from dissected subcutaneous tissue on day 42. Red and white signals represent RFP fluorescence and autofluorescence, respectively. (8D) Cells resected from a RFP positive tissue were cultured in vitro for 10 days (scale bar=400 μm).

FIGS. 9A and 9B. Two-dimensional culture of HDFs on surface of 0.5 wt % peptide hydrogels or 0.3 wt % collagen hydrogels with DMEM (9A) or FBS-supplemented DMEM (9B). Live and dead cells were visualized using calcein AM and ethidium homodimer-1, respectively (scale bar=100 μm).

FIG. 10. Using electrostatics to control protein release from peptide hydrogels. Hydrogel formed with a negatively charged peptide fiber leads to fast release of negatively charged protein, and slow, limited release of positively charged protein. Attachment of a positively charged peptide tag to the negatively charged protein leads to tunable protein release from the hydrogel, depending on the net charge of the peptide tag.

FIGS. 11A-11C. (11A) Release of EGFP analogs over 5 weeks. (11B) Average fluorescence spectra of released EGFP, normalized to pre-encapsulated stock. (11C) Predicted and experimental release for linear combination of RH2 (0.4)/RH3(0.6).

FIGS. 12A and 12B. Rheological data demonstrating shear-thin recovery of 0.5 wt. % AcVES hydrogels loaded with EGFP and selected analogs. (12A) Dynamic time sweep experiments. Hydrogels were set for 60 min, followed by 30 s of high strain, then a recovery period of 60 min. (12B) Storage moduli after 60 min. Bars outlined in black represent post shear storage moduli after 60 min recovery.

Figure 13:
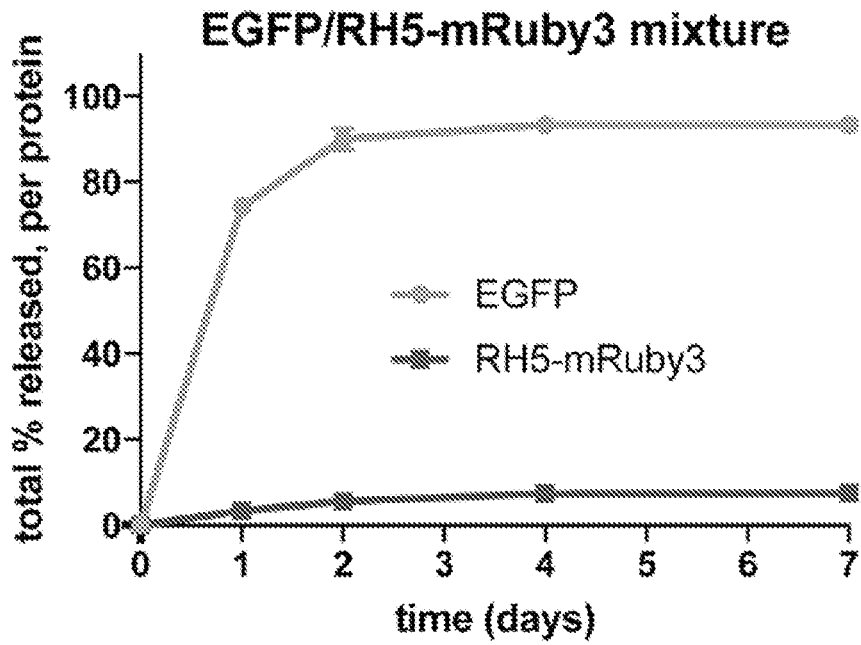

FIG. 13. Dual, staggered release of similarly charged protein from AcVES3 hydrogel. EGFP and mRuby3 have similar net charges. mRuby3 was linked to the RH5 peptide tag. An AcVES3-based hydrogel containing both RH5-mRuby3 and EGFP was generated, and protein release assayed.

Figure 14:
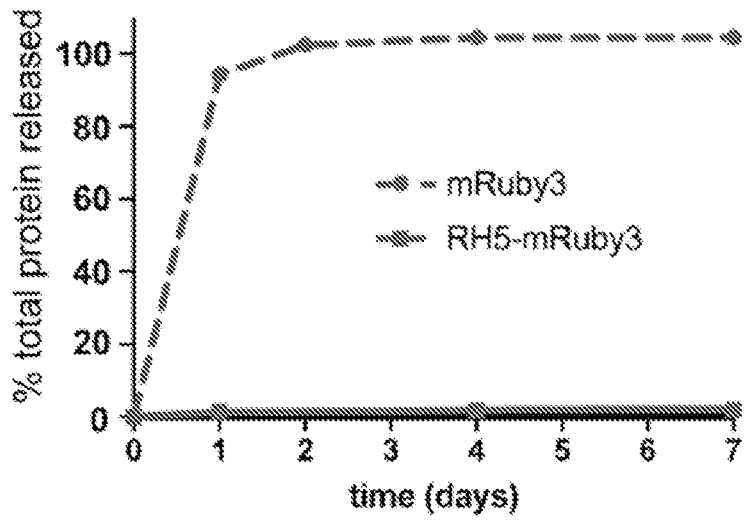

FIG. 14. In vitro release of mRuby and RH5-mRuby from AcVES3 hydrogel.

Figure 15A:
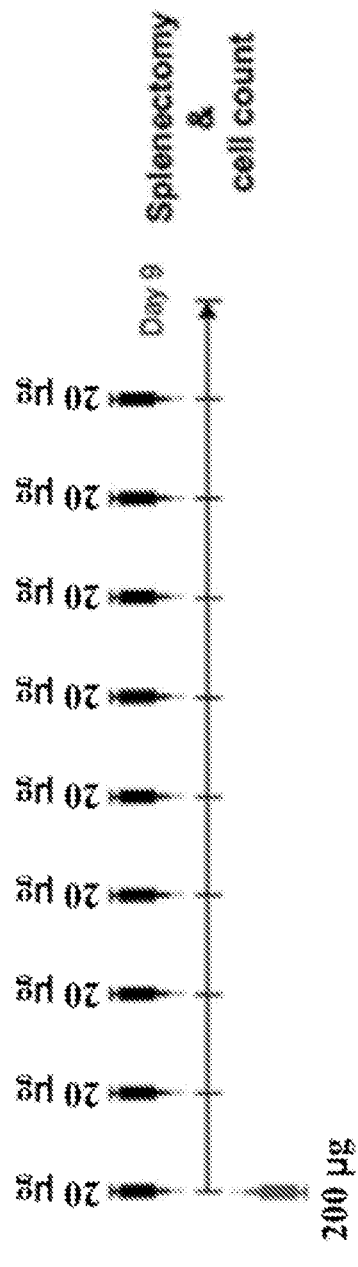
Figure 15B:
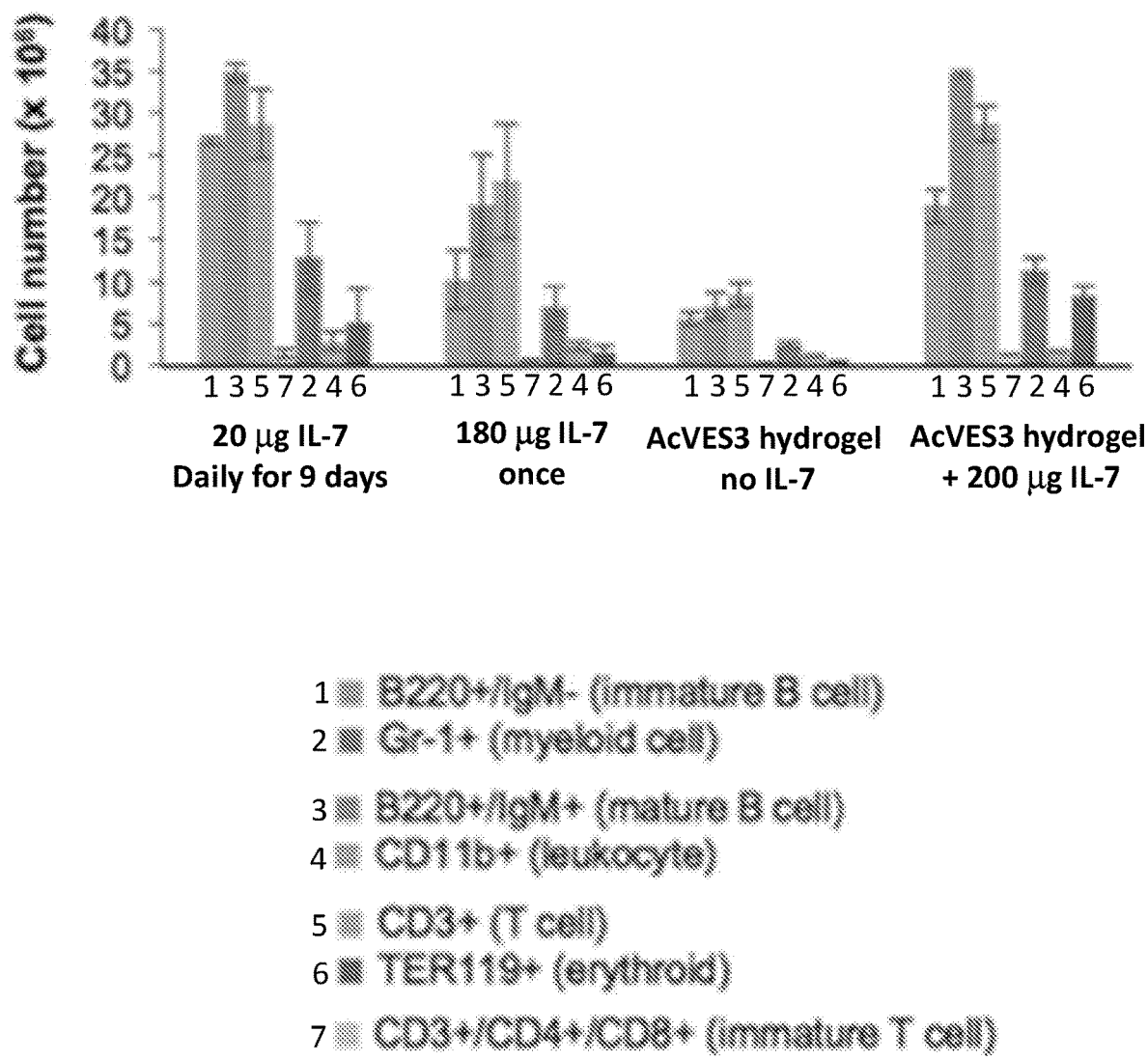

FIGS. 15A and 15B. (15A) Experimental protocol to assess lymphocyte expansion in C57BL/6 mice after daily intraperitoneal injections of IL-7 (20 µg), a single intraperitoneal IL-7 injection (180 µg), and subcutaneous injections of AcVES3 hydrogel with and without IL-7 (200 µg). There were 2-3 mice in each group. Splenocytes were isolated from the mice groups after 9 days. (15B) Spleen cell populations of mice after various treatment strategies were sorted using flow cytometry.

Figure 16A:
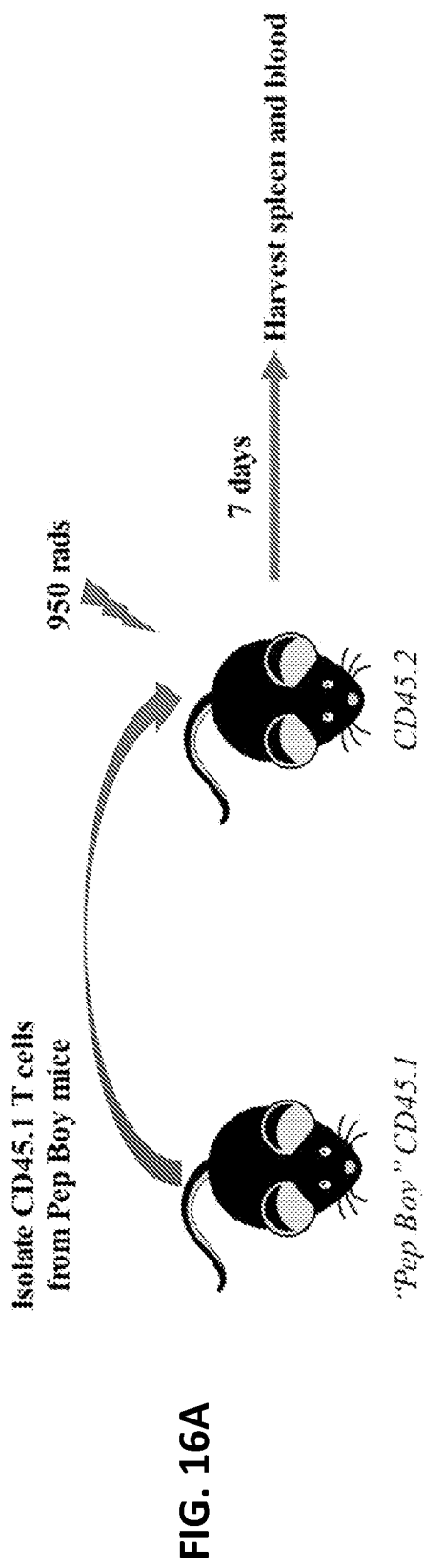
Figure 16B:
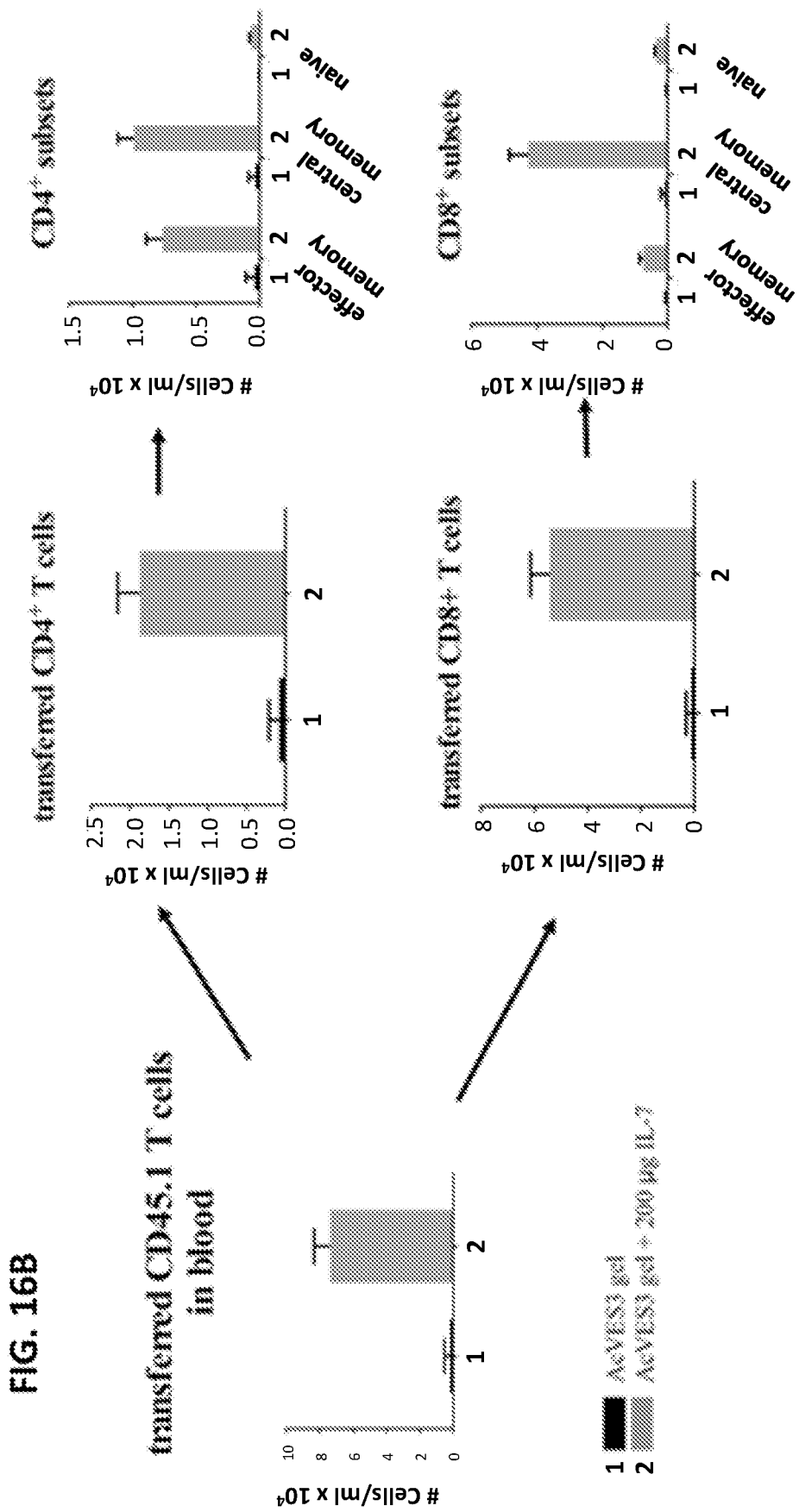

FIGS. 16A and 16B. In vivo T cell adoptive transfer with IL-7/AcVES3 hydrogel. (16A) CD45.1 T cells were extracted from spleens of "Pep Boy" mice and were purified using magnetic sorting. CD45.2 T cells mice were irradiated with 950 rads to ablate their lymphocytes and were subsequently injected with CD45.1 T cells from the Pep Boy mice. AcVES3 hydrogels with and without IL-7 were subcutaneously injected into the flanks of the CD45.2 mice and spleens and blood isolated after 7 days. (16B) Isolation and characterization of transferred CD45.1 T cells in the blood as a function of AcVES3 hydrogels with (grey bars) and without IL-7 (black bars). There was significant expansion of $CD4^+$ and $CD8^+$ T cell populations with the IL-7/AcVES3 hydrogel versus the hydrogel alone.

Figure 17:
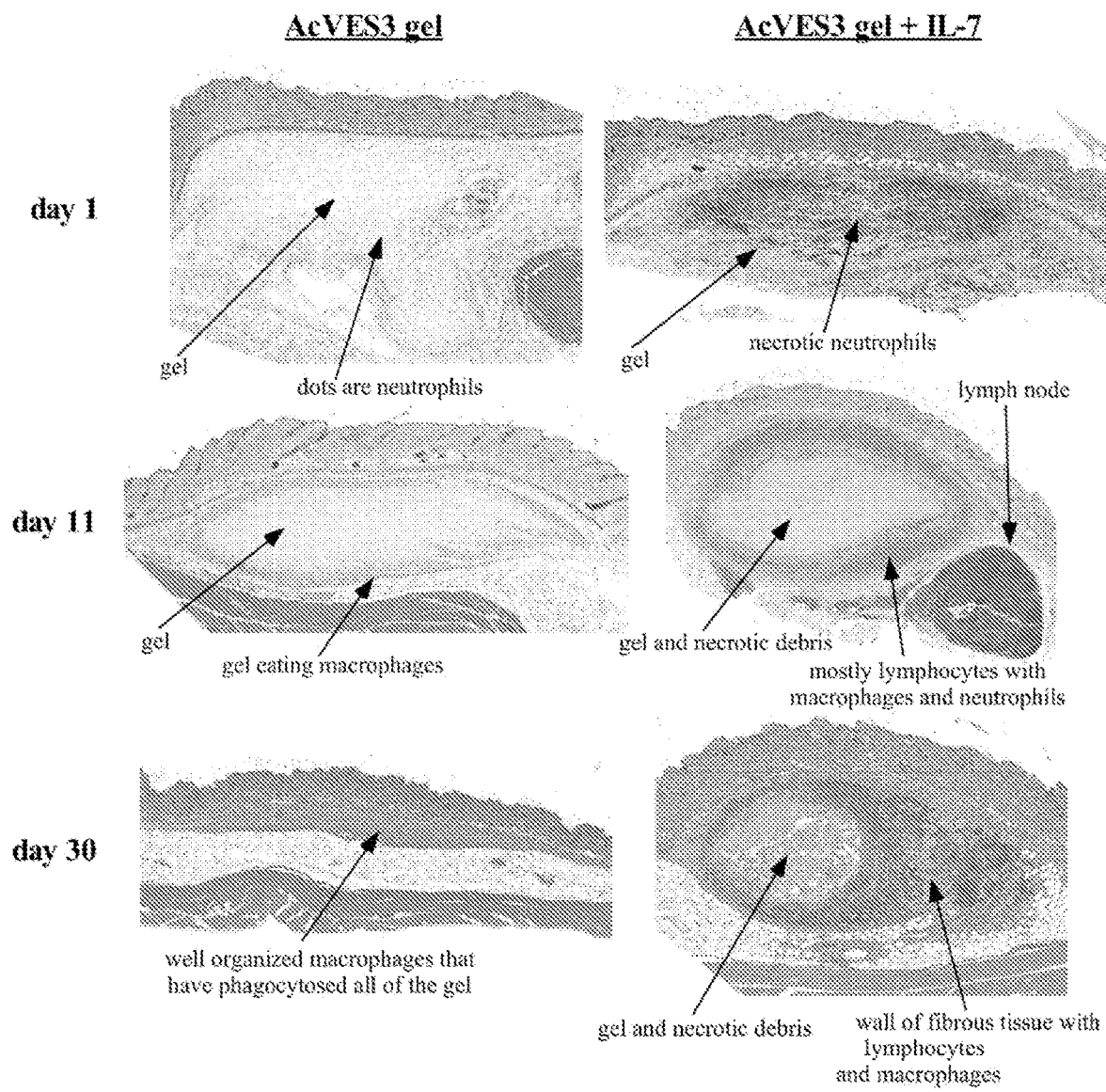

FIG. 17. Histological images of delivery of the AcVES3 hydrogel alone and with IL-7. Cross sections of subcutaneous hydrogel injections taken on days 1, 11, and 30. There were 9 animals in each group (hydrogel alone and hydrogel plus IL-7). On each respective day, 3 mice were euthanized, cells analyzed, and tissue H&E stained. The cross sections were analyzed by an expert veterinary pathologist.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~16 kb), which was created on Apr. 10, 2020, which is incorporated by reference herein.

DETAILED DESCRIPTION

Hydrogels formed from peptides disclosed herein are remarkably cytocompatible even in the absence of serum. This is surprising because prior peptide-based hydrogels typically require serum to be present to ensure cytocompatibility; proteins from the serum coat the matrix of these hydrogels, which provides a protective layer between the peptide matrix and the cells. Because of this, the prior peptide-based hydrogels are not chemically defined in that the composition of the serum protein coatings is not known, and therefore, such peptide hydrogels may not be preferred for in vivo implantation of cell-based therapeutics. In contrast, the unique charge state and hydrophilicity of the fibrils formed by the disclosed peptides (such as Ac-VES3 and AcVES3-RGDV) are believed to provide the cytocompatible properties of corresponding hydrogel. No serum proteins are needed to coat and passivate the surface of the hydrogels formed by the disclosed peptides (such as Ac-VES3 and AcVES3-RGDV), and thus the hydrogel is chemically defined.

Further, when implanted in vivo, hydrogels formed from peptides disclosed herein (such as Ac-VES3 and AcVES3-RGDV) do not elicit a lymphocytic inflammatory response, demonstrating that such hydrogels are remarkably biocompatible. In contrast, most other peptide hydrogels elicit a lymphocytic response. In light of the minimal immune background of hydrogels formed from peptides disclosed herein (such as Ac-VES3 and AcVES3-RGDV), these hydrogels are ideal materials for delivery of therapeutic proteins (such as cytokines, for example, IL-7) that modulate lymphocytic behavior.

In addition to providing superior cytocompatibility and biocompatibility, hydrogels formed from peptides disclosed herein (such as Ac-VES3 and AcVES3-RGDV) displays shear-thin/recovery mechanical properties, which allows the hydrogels and any therapeutic dispersed within the hydrogels to be delivered locally to tissue by simple syringe injection. Taken together, the cytocompatible, biocompatible, and mechanical properties of the disclosed hydrogels make them ideal for both cell and protein delivery.

A. Summary of Terms

Unless otherwise noted, technical terms are used according to conventional usage. As used herein, the singular forms "a," "an," and "the," refer to both the singular as well as plural, unless the context clearly indicates otherwise. For example, the term "a peptide" includes single or plural peptides and can be considered equivalent to the phrase "at least one peptide." As used herein, the term "comprises" means "includes." Thus, "comprising a peptide" means "including a peptide" without excluding other elements. It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

About: Unless context indicated otherwise, "about" refers to plus or minus 5% of a reference value. For example, "about" 100 refers to 95 to 105.

Administration: The introduction of a composition into a subject by a chosen route. Administration can be local or systemic. Exemplary routes of administration include, but are not limited to, oral, injection (such as subcutaneous, intramuscular, intradermal, intraperitoneal, and intravenous), sublingual, rectal, transdermal, intranasal, and vaginal routes.

Amphiphilic β-hairpin conformation: A structural conformation of a peptide or protein. The β-hairpin conformation includes two β-strands linked by a β-turn to form a "hairpin"-like shape. The structure is amphiphilic; thus, one face of the hairpin is primarily hydrophobic, and the other is primarily hydrophilic. A limited number of the side chains of hydrophobic amino acids can exist on the hydrophilic face of the hairpin and vice versa, but not so many as to change the overall amphiphilicity of the folded structure. A non-limiting example of a peptide that can fold into an amphiphilic β-hairpin conformation is provided herein as AcVES3.

Cell culture: The process by which either prokaryotic or eukaryotic cells are grown under controlled conditions. In practice the term "cell culture" has come to refer to the culturing of cells derived from multicellular eukaryotes, especially animal cells, such as mammalian cells. Mammalian cells are grown and maintained at an appropriate temperature and gas mixture (typically, 37° C., 5% $CO_2$) in a cell incubator. Culture conditions vary widely for each cell type, and variation of conditions for a particular cell type can result in different phenotypes being expressed. Aside from temperature and gas mixture, the most commonly varied factor in culture systems is the growth medium. Recipes for growth media can vary in pH, glucose concentration, growth factors, and the presence of other nutrient components. The growth factors used to supplement media are often derived from animal blood, such as calf serum.

Chimeric Antigen Receptor (CAR): An engineered T cell receptor having an extracellular antibody-derived targeting domain (such as an scFv) joined to one or more intracellular signaling domains of a T cell receptor. A "chimeric antigen receptor T cell" or "CAR T cell" is a T cell expressing a CAR, and has antigen specificity determined by the antibody-derived targeting domain of the CAR. Methods of making CARs (e.g., for treatment of cancer) are available (see, e.g., Park et al., *Trends Biotechnol.*, 29:550-557, 2011; Grupp et al., N Engl J Med., 368:1509-1518, 2013; Han et al., J. Hematol Oncol., 6:47, 2013; Haso et al., (2013) *Blood*, 121, 1165-1174; PCT Pubs. WO2012/079000, WO2013/059593; and U.S. Pub. 2012/0213783, each of which is incorporated by reference herein in its entirety.)

Consists Of: With regard to a polypeptide, a polypeptide that consists of a specified amino acid sequence does not include any additional amino acid residues, nor does it include additional non-peptide components, such as lipids, sugars or labels.

Cytokine: A generic name for a diverse group of soluble proteins and peptides which act as humoral regulators at nano- to picomolar concentrations and which, either under normal or pathological conditions, modulate the functional activities of individual cells and tissues. These proteins also mediate interactions between cells directly and regulate processes taking place in the extracellular environment. Many cytokines act as cellular survival factors by preventing programmed cell death. Non-limiting examples of cytokines include IL-2, IL-7, and IL-15.

Disperse: Distribute throughout a medium, such as a disclosed peptide hydrogel. In particular examples, cells or proteins that are dispersed in a medium are distributed evenly throughout the medium. However, dispersal of cells or proteins in a medium does not require absolute even distribution.

Fusion Protein: A single polypeptide chain including the sequence of two or more heterologous proteins, often linked by a peptide linker.

Heterologous: A heterologous peptide refers to a peptide derived from a different source or species.

Integrin Binding Peptide: A peptide having an amino acid sequence that binds to one or more integrin proteins on the surface of cells. In a non-limiting example, an integrin binding peptide is set forth as RGDV (SEQ ID NO: 5).

Isolated: An "isolated" biological molecule (such as a nucleic acid molecule, or peptide) that has been substantially separated or purified away from other biological components in the tissue or cell of the organism in which the component naturally occurs, or from contaminants or other by-products generated when a nucleic acid molecule or peptide is generate synthetically. In some embodiments, nucleic acids and peptides that have been "isolated" include nucleic acids and peptides purified by standard purification methods. The term embraces nucleic acids and peptides prepared by recombinant expression in a host cell as well as chemically synthesized nucleic acids and peptides.

Peptide: A chain of amino acids, typically less than 75 amino acids in length, such as 20-50 amino acids in length. The residues in a peptide can include post-translational or secondary modifications, such as glycosylation, sulfation or phosphorylation, as well as chemical modifications. "Peptide" applies to naturally occurring amino acid polymers and non-naturally occurring amino acid polymers, including amino acid polymers in which one or more amino acid residues are non-natural amino acids. A "residue" refers to an amino acid or amino acid mimetic incorporated in a peptide by an amide bond or amide bond mimetic. A peptide has an amino terminal (N-terminal) end and a carboxy terminal (C-terminal) end.

Typically, the amino acids making up a peptide are numbered in order, starting at the amino terminus and increasing in the direction toward the carboxy terminus of the peptide. Thus, when one amino acid is said to "follow" another, that amino acid is positioned closer to the carboxy terminal end of the peptide than the preceding amino acid.

Peptide hydrogel: A colloid gel including an internal phase and a dispersion medium, in which an aqueous solution is the dispersion medium and a self-assembled network of peptides is the internal phase. The peptides in the hydrogel are self-assembled and are folded into an amphiphilic β-hairpin conformation in the fibrillar network that forms the internal phase of the hydrogel. The peptide hydrogels disclosed herein are made using peptides that form an amphiphilic β-hairpin conformation in an aqueous solution comprising 150 mM NaCl and a pH of 7.4 at 25-37° C. Thus, an aqueous solution containing 2% w/v of a disclosed peptide and 150 mM NaCl and a pH of 7.4 forms a peptide hydrogel comprising a fibrillar network of a plurality of the peptide when incubated at 25-37° C. in a container. Peptide hydrogels include a sufficient elastic modulus or stiffness that allows them to maintain shape. In several embodiments, the peptide hydrogel has an elastic modulus of 40 Pascal or greater. Peptide hydrogels formed from the disclosed self-assembled peptides in an amphiphilic β-hairpin conformation can be characterized by shear-thin/recovery rheological properties. The hydrogel undergoes a gel-sol phase transition upon application of shear stress, and a sol-gel phase transition upon removal of the shear stress. Thus, application of shear stress converts the solid-like gel into a viscous gel capable of flow, and cessation of the shear results in gel recovery. General information concerning peptide hydrogels having shear-thin/recovery rheological properties and methods of making same is provided, for example, in Sathaye, et al. Biomacromolecules, 2014, 15(11):3891-3900; Hule et al., 2008, Faraday Discuss, 139:251-420. In several embodiments, the peptide hydrogel can be a sterile hydrogel prepared with physiological and non-toxic dispersion medium for use to deliver a therapeutic protein or cells to a subject.

Peptide Linker: A peptide of 20 or fewer amino acids that is used to fuse two heterologous polypeptides into one contiguous polypeptide chain. Non-limiting examples of peptide linkers include glycine linkers, serine linkers, and glycine-serine linkers, such as a 10 amino acid glycine-serine linker Unless context indicates otherwise, reference to "linking" or "fusing" a first polypeptide and a second polypeptide (or to two polypeptides "linked" or "fused" together) by peptide linker refers to covalent linkage of the first and second polypeptides to the N- and C-termini of the peptide linker to form a single polypeptide chain.

Peptide tag: A peptide sequence that is attached (for instance through genetic engineering) to another peptide or a protein, to provide a function to the resultant fusion. Peptide tags are usually relatively short in comparison to a protein to which they are fused. Usually a peptide tag will be no more than about 20 amino acids in length. Peptide tags confer one or more different functions to a fusion protein (thereby "functionalizing" that protein). In several embodiments described herein, a peptide tag having a net positive charge is fused to a protein having a net negative charge to delay release of the protein from a negatively charged peptide hydrogel as described herein.

Protein: Any chain of amino acids, regardless of length or post-translational modification (e.g., glycosylation or phosphorylation). "Protein" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. A protein has an amino terminal (N-terminal) end and a carboxy terminal (C-terminal) end.

Polypeptide and protein modifications: The present disclosure includes synthetic peptides, as well as derivatives (chemically functionalized polypeptide molecules obtained starting with the disclosed polypeptide sequences) and variants (homologs) of peptides described herein. The peptides disclosed herein include a sequence of amino acids that can include L- and/or D-amino acids, naturally occurring and otherwise.

Peptides can be modified by a variety of chemical techniques to produce derivatives having essentially the same activity as the unmodified polypeptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the polypeptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the polypeptide side chains can be converted to $C_1$-$C_{16}$ alkoxy or to a $C_1$-$C_{16}$ ester using well-recognized techniques. Phenyl and phenolic rings of the polypeptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the polypeptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the polypeptides of this disclosure to select and provide conformational constraints to the structure that result in enhanced stability. For example, a C- or N-terminal cysteine can be added to the polypeptide, so that when oxidized the polypeptide will contain a disulfide bond, generating a cyclic polypeptide. Other polypeptide cyclizing methods include the formation of thioethers and carboxyl- and amino-terminal amides and esters.

Subject: Living multi-cellular vertebrate organisms, a category that includes human and non-human mammals. In one example, a subject is a human.

Therapeutic protein: A protein capable of inducing a desired therapeutic or prophylactic effect when properly administered to a subject, alone or in combination with another therapeutic agent(s) or pharmaceutically acceptable carriers. Non-limiting examples of therapeutic proteins include, but are not limited to, antibodies, cytokines (for example, IL-7, IL-2, IL-15), blood factors (for example, Factor VIII and Factor IX), and hormones (for example, insulin, glucagon, growth hormone, gonadotropins).

B. Peptides, Peptide Hydrogels, and their Use

Peptides

This disclosure provides peptides that, under appropriate conditions (e.g., 2.0% w/v peptide in 50 mM Bis Tris Propane, pH 7.4, 150 mM NaCl, at 25° C.), can fold into an amphiphilic β-hairpin conformation comprising a β-turn, two β-strands, a hydrophobic face, and a hydrophilic face. Under the appropriate conditions, the folded peptides self-assemble into a fibrillar network and cause a solution containing the network to undergo a sol-gel phase transition to form a hydrogel.

The resultant hydrogel is mechanically rigid and displays shear-thinning/recovery behavior. This characteristic provides a free flowing suspension during the application of shear and complete reformation of the gel network (self-healing) after cessation of the shear. This combination of shear thinning and self-healing allows material formation in a spatially resolved manner. For example, in some embodiments, one of ordinary skill in the art can inject (shear thin) a pre-formed hydrogel containing a heterologous therapeutic protein (such as IL-7) or a heterologous cell (such as a CAR T-cell) into a target location in a subject where it self heals and reforms the hydrogel containing the heterologous therapeutic protein or a heterologous cell. The shear stress converts the gel to a lower viscosity, flowable fluid. The shear stress is relieved when the fluid exits the syringe and the gel quickly self-heals, recovering its original mechanical rigidity. This shear-thinning/recovery mechanism allows the hydrogel to be easily delivered by syringe to the target location in the subject.

Figure 1B:
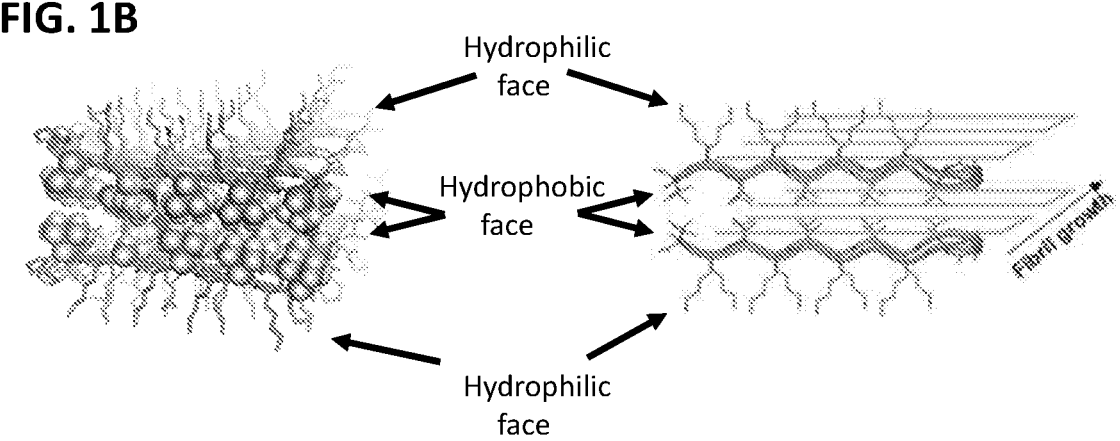

As illustrated in FIG. 1, the β-strand regions of the hairpin contain alternating sequences of hydrophobic (e.g., valine) and hydrophilic (charged) residues (e.g., glutamate) such that in the folded state, one face (e.g., the valine-rich face) of the peptide is hydrophobic and the opposing face (e.g., the glutamate rich face) is lined with negatively charged side chains and is hydrophilic. This amphiphilic arrangement facilitates inter-molecular peptide interactions, and the fibril arrangement necessary for hydrogel formation.

Self-assembly of monomeric hairpins is facilitated facially by hydrophobic association of the hydrophobic faces of folded hairpins and laterally via H-bond formation and hydrophobic van der Waals contacts between neighboring hairpins. Detailed knowledge of these parameters allows control the self-assembly process and thus the ultimate hydrogel material properties. For example, under folding conditions peptides may adopt a desired secondary structure (e.g., may adopt an amphiphilic β-hairpin structure where one face of each β-strand in the hairpin is lined with hydrophobic residues and the other face is lined with hydrophilic residues). For example, intramolecular folding is dictated by the alleviation of charge density on the hydrophilic face upon folding, the formation of intramolecular hydrophobic van der Waals interactions, the formation of intramolecular hydrogen bonds between β-strands within the hairpin, and the turn propensity of the β-turn sequence included in the peptide, see, e.g., FIG. 1.

Thus, peptides for use in the disclosed hydrogels can be constructed to have desired characteristics by varying one or more of at least the following parameters: 1) electrostatics, for example, by varying the charge within the peptide intramolecular folding and self-assembly rates can be varied; 2) van der Waals interactions, for example, constructing peptides having varying a) lateral and facial intermolecular hydrophobic interactions and/or b) intramolecular hydrophobic interactions, allows varying the folding and self-assembly of the peptides as well as the material properties of the hydrogel; 3) hydrogen bonding, for example peptides may be constructed with varying a) intramolecular and/or b) intermolecular hydrogen bond formation to vary the folding, self-assembly and final material properties; and 4) turn sequence, for example, the turn region of peptides of the invention may be designed to control folding and thus trigger self-assembly.

In several embodiments, the disclosed peptide includes high β-sheet propensity residues flanking an intermittent four residue turn sequence. Polar and apolar residues may be arranged sequentially in the strand regions to afford amphiphilic surfaces when the peptide is folded in a β-hairpin conformation. For the four residue turn sequence, the peptide typically includes four residues (termed i, i+1, i+2, and i+3) that form a type II' β-turn. In the disclosed AcVES3 peptide, these four residues are V$^D$PPT, and the type II' β-turn is defined by the dihedral angles (Phi and Psi) adopted by the $^D$PP portion of the turn sequence, where '$^D$' denotes D-stereochemistry of the first proline residue. The preferred Phi and Psi dihedral angles (degrees) that define a type II' turn are: residue i+1 (60,–120); residue i+2 (–80,0). However, these values can vary by +/–20 degrees and the peptide can still form the appropriate β-turn structure In one particular embodiment, AcVES3, a 20-residue peptide is composed of high β-sheet propensity valine, glutamate, and serine residues flanking an intermittent tetrapeptide-V$^D$PPT-designed to adopt type-IF β-turn structure. In addition to incorporating local design elements to stabilize hairpin structure, nonlocal effects were also considered by arranging the polar and apolar residues flanking the β-turn in an alternating fashion to favor β-hairpin formation in the self-assembled state. In addition, a β-branched residue was placed at the i-position of the turn to enforce a trans prolyl amide bond geometry at the i+1 position. This design element ensures that under folding conditions, intramolecular folding of monomeric hairpins is favored prior to self-assembly. A cis prolyl bond, which is designed against, could result in the presentation of individual β-strands within each monomer in an extended conformation. Peptides capable of adopting both cis and trans conformers could undergo indiscriminant self-association of extended and correctly folded monomers and may be actively designed against.

In some embodiments, the peptide comprises or consists of an amino acid sequence set forth as:

(1)
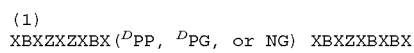
XBXZXZXBX($^D$PP, $^D$PG, or NG) XBXZXBXBX wherein each X is independently selected from any one of L, I, T, and V; each B is independently selected from any one of D, E, and S; each Z is independently selected from any one of D, E, Q, N, T, K, R, and S; the $^D$P is a proline that is a D amino acid; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (1), the C-terminus of the peptide is amidated and the N-terminus of the peptide is acetylated. For example, the peptide comprises or consists of an amino acid sequence set forth as:

(1a)
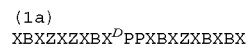
XBXZXZXBX$^D$PPXBXZXBXBX wherein each X is independently selected from any one of L, I, T, and V; each B is independently selected from any one of D, E, and S; each Z is independently selected from any one of D, E, Q, N, T, K, R, and S; the $^D$P is a proline that is a D amino acid; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (1a), the C-terminus of the peptide is amidated and the N-terminus of the peptide is acetylated. For example, the peptide comprises or consists of an amino acid sequence set forth as:

(1b)
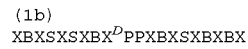
XBXSXSXBX$^D$PPXBXSXBXBX wherein each X is independently selected from any one of L, I, T, and V; each B is independently selected from any one of D, E, and S; the $^D$P is a proline that is a D amino acid; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (1b), the C-terminus of the peptide is amidated and the N-terminus of the peptide is acetylated. In another example, the peptide comprises or consists of an amino acid sequence set forth as:

(1c)
XEXSXSXEX$^D$PPXEXSXEXEX wherein each X is independently selected from any one of L, I, T, and V; the $^D$P is a proline that is a D amino acid; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (1c), the C-terminus of the peptide is amidated and the N-terminus of the peptide is acetylated. In another example, the peptide comprises or consists of an amino acid sequence set forth as:

(1d)
VEVSVSVEV$^D$PPTEVSVEVEV wherein the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (1d), the C-terminus of the peptide is amidated and the N-terminus of the peptide is acetylated.

In some embodiments, the peptide comprises or consists of an amino acid sequence set forth as:

(2a)
XBXZXZXBX$^D$PGXBXZXBXBX wherein each X is independently selected from any one of L, I, T, and V; each B is independently selected from any one of D, E, and S; each Z is independently selected from any one of D, E, Q, N, T, K, R, and S; the $^D$P is a proline that is a D amino acid; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (2a), the C-terminus of the peptide is amidated and the N-terminus of the peptide is acetylated. For example, the peptide comprises or consists of an amino acid sequence set forth as:

(2b)
XBXSXSXBX$^D$PGXBXSXBXBX wherein each X is independently selected from any one of L, I, T, and V; each B is independently selected from any one of D, E, and S; the $^D$P is a proline that is a D amino acid; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (2b), the C-terminus of the peptide is amidated and the N-terminus of the peptide is acetylated. In another example, the peptide comprises or consists of an amino acid sequence set forth as:

(2c)
XEXSXSXEX$^D$PGXEXSXEXEX wherein each X is independently selected from any one of L, I, T, and V; the $^D$P is a proline that is a D amino acid; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (2c), the C-terminus of the peptide is amidated and the N-terminus of the peptide is acetylated. In another example, the peptide comprises or consists of an amino acid sequence set forth as:

(2d)
VEVSVSVEV$^D$PGTEVSVEVEV wherein the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (2d), the C-terminus of the peptide is amidated and the N-terminus of the peptide is acetylated.

In some embodiments, the peptide comprises or consists of an amino acid sequence set forth as:

(3a)
(SEQ ID NO: 1)
XBXZXZXBXNGXBXZXBXBX wherein each X is independently selected from any one of L, I, T, and V; each B is independently selected from any one of D, E, and S; each Z is independently selected from any one of D, E, Q, N, T, K, R, and S; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (3a), the C-terminus of the peptide is amidated and the N-terminus of the peptide is acetylated. For example, the peptide comprises or consists of an amino acid sequence set forth as:

(3b)
(SEQ ID NO: 2)
XBXSXSXBXNGXBXSXBXBX wherein each X is independently selected from any one of L, I, T, and V; each B is independently selected from any one of D, E, and S; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (3b), the C-terminus of the peptide is amidated and the N-terminus of the peptide is acetylated.

In another example, the peptide comprises or consists of an amino acid sequence set forth as:

(3c)
(SEQ ID NO: 3)
XEXSXSXEXNGXEXSXEXEX wherein each X is independently selected from any one of L, I, T, and V; the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (3c), the C-terminus of the peptide is amidated and the N-terminus of the peptide is acetylated. In another example, the peptide comprises or consists of an amino acid sequence set forth as:

(3d)
(SEQ ID NO: 4)
VEVSVSVEVNGTEVSVEVEV wherein the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some embodiments of peptide (3d), the C-terminus of the peptide is amidated and the N-terminus of the peptide is acetylated.

In some embodiments, the peptide is set forth as any one of:

```
(1)
Ac-XBXZXZXBX(DPP, DPG, or NG) XBXZXBXBX-NH2

(1a)
Ac-XBXZXZXBXDPPXBXZXBXBX-NH2

(1b)
Ac-XBXSXSXBXDPPXBXSXBXBX-NH2

(1c)
Ac-XEXSXSXEXDPPXEXSXEXEX-NH2

(1d)
Ac-VEVSVSVEVDPPTEVSVEVEV-NH2

(2a)
Ac-XBXZXZXBXDPGXBXZXBXBX-NH2

(2b)
Ac-XBXSXSXBXDPGXBXSXBXBX-NH2

(2c)
Ac-XEXSXSXEXDPGXEXSXEXEX-NH2

(2d)
Ac-VEVSVSVEVDPGTEVSVEVEV-NH2

(3a)
                                    (SEQ ID NO: 1)
Ac-XBXZXZXBX NGXBXZXBXBX-NH2

(3b)
                                    (SEQ ID NO: 2)
Ac-XBXSXSXBX NGXBXSXBXBX-NH2
```

```
(3c)
                                    (SEQ ID NO: 3)
Ac-XEXSXSXEX NGXEXSXEXEX-NH2

(3d)
                                    (SEQ ID NO: 4)
Ac-VEVSVSVEV NGTEVSVEVEV-NH2.
``` wherein each X, if present, is independently selected from any one of L, I, T, and V; each B, if present, is independently selected from any one of D, E, and S; each Z, if present, is independently selected from any one of D, E, Q, N, T, K, R, and S; the $^{D}$P is a proline that is a D amino acid; and the peptide is in an amphiphilic β-hairpin conformation when dissolved at 2.0% w/v in 50 mM Bis Tris Propane, pH 7.4, 150 mM NaCl, at 25° C.

In a preferred embodiment, the peptide is set forth as:

```
AcVES3
Ac-VEVSVSVEVDPPTEVSVEVEV-NH2
```

Linkage to an Integrin Binding Peptides

In several embodiments, any of the amphiphilic β-hairpin peptides disclosed herein can be fused to an integrin binding peptide for production of peptide hydrogels that provide a matrix for cell growth and proliferation, and which can be used to administer cells to a subject. The presence of the integrin binding peptide in the hydrogel increases cell binding to the hydrogel matrix, which increases retention of the cells in the matrix. Trigger-dependent gelation of the peptide allows homogeneous cell encapsulation and its integrin-binding activity provides proliferation of encapsulated anchorage-dependent cells, though the system also may be applicable to anchorage-independent cells. The expanded cells can be directly delivered with the hydrogel to the target tissue site by syringe injection due to the shear-thinning recovery property of the hydrogel, and the delivered cells can be retained in the target tissue over an extended period of time.

In some embodiments, the peptide comprises or consists of an amino acid sequence set forth as Peptide (1) described above fused to the integrin binding peptide (such as one of RGDV (SEQ ID NO: 5), KQAGDV (SEQ ID NO: 6), RLD, KRLDGS (SEQ ID NO: 7), LDV, IDS, LET, IET, YYDLR (SEQ ID NO: 8), or FYFDLR (SEQ ID NO: 9), wherein the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. For example, the peptide comprises an amino acid sequence set forth as Peptide (1a), Peptide (1b), peptide (1c), peptide (1d), Peptide (2a), Peptide (2b), peptide (2c), peptide (2d), Peptide (3a), Peptide (3b), peptide (3c), peptide (3d), described above fused to the integrin binding peptide (such as one of RGDV (SEQ ID NO: 5), KQAGDV (SEQ ID NO: 6), RLD, KRLDGS (SEQ ID NO: 7), LDV, IDS, LET, IET, YYDLR (SEQ ID NO: 8), or FYFDLR (SEQ ID NO: 9), wherein the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. In some such embodiments, the C-terminus of the peptide is amidated and the N-terminus of the peptide is acetylated.

In some embodiments, the peptide comprises or consists of an amino acid sequence set forth as Peptide (1) described above fused to the integrin binding peptide (such as one of RGDV (SEQ ID NO: 5), KQAGDV (SEQ ID NO: 6), RLD, KRLDGS (SEQ ID NO: 7), LDV, IDS, LET, IET, YYDLR (SEQ ID NO: 8), or FYFDLR (SEQ ID NO: 9) by a peptide linker, wherein the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. For example, the peptide comprises an amino acid sequence set forth as Peptide (1a), Peptide (1b), peptide (1c), peptide (1d), Peptide (2a), Peptide (2b), peptide (2c), peptide (2d), Peptide (3a), Peptide (3b), peptide (3c), peptide (3d), described above fused to the integrin binding peptide (such as one of RGDV (SEQ ID NO: 5), KQAGDV (SEQ ID NO: 6), RLD, KRLDGS (SEQ ID NO: 7), LDV, IDS, LET, IET, YYDLR (SEQ ID NO: 8), or FYFDLR (SEQ ID NO: 9) by the peptide linker, wherein the C-terminus of the peptide is amidated or free carboxylic acid; the N-terminus of the peptide is acetylated or free amine; the peptide is no more than 50 amino acids in length, and the peptide is in an amphiphilic β-hairpin conformation when dissolved at 2.0% w/v in 50 mM Bis Tris Propane, pH 7.4, 150 mM NaCl, at 25° C. The peptide linker can be, for example, a glycine linker (such as GGGG, SEQ ID NO: 10), a serine linker, or a glycine-serine linker. In some such embodiments, the C-terminus of the peptide is amidated and the N-terminus of the peptide is acetylated.

In a preferred embodiment, the peptide fused to the integrin binding peptide is set forth as:

AcVES3-RGDV
Ac-VEVSVSVEV$^D$PPTEVSVEVEVGGGRGDV-NH$_2$

Peptides for use in the disclosed embodiments can be peptides from about 20 to about 75 residues (e.g., from about 20 to about 50 residues, from about 20 to about 40 residues, from about 20 to about 30 residues, from about 20 to about 25 residues, from about 20 to about 50 residues, from about 20 to about 40 residues, from about 20 to about 30 residues, or from about 20 to about 25 residues ("about" refers to plus or minus 2 residues). In some embodiments, the peptides for use in the disclosed embodiments can be from 20 to 75 residues (e.g., from 20 to 50 residues, from 20 to 40 residues, from 20 to 30 residues, from 20 to 25 residues, from 20 to 50 residues, from 20 to 40 residues, from 20 to 30 residues, or from 20 to 25 residues). In some embodiments, the peptide can be no more than 50 residues, such as no more than 30 residues or no more than 20 residues. In additional embodiments, the peptide can be 20, 25, 30, 35, 40, 45, or 50, residues in length. In some embodiments, the peptide can be 20 amino acids in length.

The disclosed peptides, and modified versions thereof can be synthesized using any appropriate technique, such as automated solid phase procedures. The disclosed peptides may incorporate one or more modified amino acid residues (e.g., D-amino acids, homologs of naturally occurring amino acids, amino acids with modified side chains, etc.). Exemplary techniques and procedures for solid phase synthesis are described in *Solid Phase Peptide Synthesis: A Practical Approach*, by E. Atherton and R. C. Sheppard, published by IRL, Oxford University Press, 1989. Alternatively, apelin-36 (42-57) peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am. Chem. Soc.* 116: 4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing the apelin-36 (42-57) peptides of the disclosure are described in Nakagawa et al., *J. Am. Chem. Soc.* 107: 7087-7092, 1985.

Additional exemplary techniques for peptide synthesis are taught by Bodanszky, M. and Bodanszky, A., *The Practice of Peptide Synthesis*, Springer Verlag, New York, 1994; and by Jones, J., *Amino Acid and Peptide Synthesis*, 2nd ed., Oxford University Press, 2002. The Bodanszky and Jones references detail the parameters and techniques for activating and coupling amino acids and amino acid derivatives. Moreover, the references teach how to select, use and remove various useful functional and protecting groups. Peptides of the disclosure can also be readily purchased from commercial suppliers of synthetic peptides once the supplied is provided with the sequence of the peptide. Such suppliers include, for example, Advanced ChemTech (Louisville, Ky.), Applied Biosystems (Foster City, Calif.), Anaspec (San Jose, Calif.), and Cell Essentials (Boston, Mass.).

Following synthesis, exemplary techniques for peptide purification include reverse phase chromatography, high performance liquid chromatography, ion exchange chromatography, size exclusion chromatography, affinity chromatography, and gel electrophoresis. The actual conditions used to purify a particular peptide, or a modified form thereof, will depend, in part, on synthesis strategy and on factors such as net charge, hydrophobicity, hydrophilicity, and the like.

Peptide Hydrogels

As discussed above, the disclosed amphiphilic β-hairpin peptides can be used to make a peptide hydrogel. The resultant hydrogel is mechanically rigid and displays shear-thinning/recovery behavior. This characteristic provides a free flowing suspension during the application of shear and complete reformation of the gel network (self-healing) after cessation of the shear. This combination of shear thinning and self-healing allows material formation in a spatially resolved manner. For example, in some embodiments, one of ordinary skill in the art can inject (shear thin) a pre-formed hydrogel containing a heterologous therapeutic protein (such as IL-7) or a heterologous cell (such as a CAR T-cell) into a target location in a subject where it self heals and reforms the hydrogel containing the heterologous therapeutic protein or a heterologous cell. The shear stress converts the gel to a lower viscosity, flowable fluid. The shear stress is relieved when the fluid exits the syringe and the gel quickly self-heals, recovering its original mechanical rigidity. This shear-thinning/recovery mechanism allows the hydrogel to be easily delivered by syringe to the target location in the subject.

Peptide hydrogels based on a disclosed peptide can readily be made by preparing an aqueous solution comprising one or more amphiphilic β-hairpin peptides as disclosed herein and altering one or more characteristics of the solution, wherein a hydrogel is formed. The characteristic altered may be any characteristic that results in formation of a hydrogel upon its alteration. Suitable examples include, but are not limited to, ionic strength, temperature, concentration of a specific ion, and pH. In particular embodiments, the character altered may be the pH of the solution. The disclosed peptides form a hydrogel at a pH of about 7 or higher. Increasing pH and increasing ionic strength both encourage hydrogel formation, and the two effects are roughly additive. Thus, the lower the pH, the higher the salt concentration necessary for hydrogel formation. In some embodiments, the hydrogel can be formed in a container (such as a syringe), for example a closed container.

In some embodiments, altering one or more characteristic of the solution results in a salt concentration of from about 10 mM to about 400 mM, such as about 50 to about 300 mM, about 100 to about 200 mM, or about 150 mM. Any salt may be used, for example, KCl, NaCl, $MgCl_2$, KF, $MgSO_4$, etc. In one embodiment, the salt may be NaCl. In some embodiments, the solution may have a desired pH, for example, a pH of from about 7 to about 9, a pH of from about 7.5 to about 8.5, a pH of from about 7.0 to about 8.0, or a pH of about 7.4, which may stay the same or be changed upon formation of the hydrogel.

In one non-limiting example, the hydrogel is formed in 50 mM Bis Tris Propane (BTP), 150 mM NaCl, pH 7.4. Any buffer system can be used except phosphate based buffer systems, as phosphate buffers are known to precipitate β-hairpin peptides. Accordingly, peptide hydrogels including the disclosed peptides can simply be formed by, for example, adding buffer of appropriate ionic strength to an aqueous solution of unfolded peptide; drawing the resulting solution into a syringe; and allowing it to gel at 25° C. directly in the syringe.

The disclosed hydrogels are well hydrated solid materials and have a stiffness greater than 40 Pascal (Pa), as measured by the storage modulus G' at a strain of 0.2%. Above approximately 40 Pa the material is a self-supporting solid gel material. The stiffness can reach greater than 10,000 Pa at higher peptide concentration. The hydrogels typically contain at least 0.5 wt % peptide in an aqueous medium. For example, the disclosed hydrogel may have varying amounts of solid (peptide) material. For example, hydrogels may be formed comprising a percent by weight of peptide of from about 0.25% w/v to about 4.0% w/v, from about 0.25% w/v to about 3.0% w/v, from about 0.25% w/v to about 2.0% w/v, from about 0.25% w/v to about 1.0% w/v, from about 0.5% w/v to about 4.0% w/v, from about 0.5% w/v to about 3.0% w/v, from about 0.5% w/v to about 2.0% w/v, from about 0.5% w/v to about 1.0% w/v, from about 1.0% w/v to about 4.0% w/v, from about 1.0% w/v to about 3.0% w/v, from about 1.0% w/v to about 2.0% w/v, from about 2.0% w/v to about 4.0% w/v, or from about 2.0% w/v to about 3.0% w/v.

In one aspect, the amount by weight of peptide and the kinetics of gelation may be varied to produce a hydrogel having a desired modulus (stiffness). Hydrogels of the invention may have a modulus from about 40 Pascal (Pa) to about 50,000 Pa, from about 40 Pa to about 25,000 Pa, from about 40 Pa to about 10,000 Pa, from about 40 Pa to about 5,000 Pa, from about 40 Pa to about 1,000 Pa, from about 40 Pa to about 500 Pa, from about 40 Pa to about 100 Pa, from about 100 Pa to about 50,000 Pa, from about 100 Pa to about 25,000 Pa, from about 100 Pa to about 10,000 Pa, from about 100 Pa to about 5,000 Pa, from about 100 Pa to about 2,000 Pa, from about 100 Pa to about 1,000 Pa, from about 100 Pa to about 500 Pa, or from about 100 Pa to about 250 Pa.

Peptide Hydrogels Including Heterologous Proteins

In some embodiments, the disclosed peptide hydrogel includes one or more heterologous proteins (such as one or more therapeutic proteins) dispersed within the hydrogel. Non-limiting examples of therapeutic proteins that can be included in the peptide hydrogel include antibodies, cytokines (for example, IL-7, IL-2, IL-15), blood factors (for example, Factor VIII and Factor IX), and hormones (for example, insulin, glucagon, growth hormone, gonadotropins).

In a preferred embodiment, the peptide hydrogel (such as an AcVES3 peptide hydrogel) includes IL-7 dispersed within the hydrogel. Full human IL-7 sequence is set forth in Genbank NP_000871.1 (incorporated by reference herein), and as:

```
                                      (SEQ ID NO: 11)
MFHVSFRYIFGLPPLILVLLPVASSDCDIEGKDGKQYESVLMVSIDQLLD

SMKEIGSNCLNNEFNFFKRHICDANKEGMFLFRAARKLRQFLKMNSTGDF

DLHLLKVSEGITILLNCTGQVKGRKPAALGEAQPIKSLEENKSLKEQKKL

NDLCFLKRLLQEIKTCWNKILMGTKEH
```

Typically, the human IL-7 protein included in the peptide hydrogel is the mature human IL-7 sequence, not including the signal peptide, which is set forth as:

```
                      (residues 26-177 of SEQ ID NO: 11)
DCDIEGKDGKQYESVLMVSIDQLLDSMKEIGSNCLNNEFNFFKRHICDA

NKEGMFLFRAARKLRQFLKMNSTGDFDLHLLKVSEGTTILLNCTGQVKG

RKPAALGEAQPTKSLEENKSLKEQKKLNDLCFLKRLLQEIKTCWNKILM

GTKEH
```

The human IL-7 protein included in the peptide hydrogel can be glycosylated, or not glycosylated. For example, unglycosylated IL-7 protein produced in bacteria can be included in the hydrogel.

Any appropriate amount of protein (e.g., unglycosylated mature human IL-7) can be included in the hydrogel. For example, the hydrogel includes from 0.001 to 10 mg/mL heterologous protein dispersed within the hydrogel, such as from 0.001 to 10 mg/mL, from 0.01 to 10 mg/mL, from 0.1 to 10 mg/mL, from 1.0 to 10 mg/mL, from 0.001 to 5 mg/mL, from 0.01 to 5 mg/mL, from 0.1 to 5 mg/mL, from 1.0 to 5 mg/mL, from 0.001 to 1 mg/mL, from 0.01 to 1 mg/mL, or from 0.1 to 1 mg/mL heterologous protein dispersed within the hydrogel. In some embodiments, the hydrogel includes up to 10 mg/mL heterologous protein dispersed within the hydrogel, such as up to 5 mg/mL, up to 1 mg/mL, up to 0.1 mg/mL, or up to 0.01 mg/mL heterologous protein dispersed within the hydrogel.

The amphiphilic β-hairpin peptides disclosed herein are anionic. Accordingly, in typical embodiments involving a heterologous protein encapsulated within the peptide hydrogel, the heterologous protein has a net negative charge to prevent binding to the hydrogel matrix and protein denaturation. Depending on the heterologous protein, the net negative charge may lead to a relatively short retention time in the peptide hydrogel. In some embodiments, the heterologous protein included in the peptide hydrogel is fused to a peptide tag having a net positive charge to increase retention of the heterologous protein in the anionic hydrogel. For example, the peptide tag comprises from 2-10 arginine or lysine residues or a mixture thereof. Non-limiting examples of such peptide tags include the RH1 (G(RH)$_1$R), SEQ ID NO: 12), RH2 (G(RH)$_2$R), SEQ ID NO: 13), RH3 (G(RH)$_3$R), SEQ ID NO: 14), RH4 (G(RH)$_4$R), SEQ ID NO: 15), RH5 (G(RH)$_5$R), SEQ ID NO: 16), and RH6 (G(RH)$_6$R), SEQ ID NO: 17) tags disclosed herein. In other embodiments, the heterologous protein is fused to a peptide tag having a net negative charge that decreases retention of the heterologous protein in the anionic hydrogel. For example, the peptide tag comprises from 2-10 aspartic acid or glutamic acid residues or a mixture thereof.

In several embodiments, the peptide tag is fused to the amphiphilic β-hairpin peptide by a peptide linker, such as a glycine linker, and serine linker, or a glycine-serine linker (for example, GGSGSGGSGS, SEQ ID NO: 18).

Peptide hydrogels including a heterologous protein can be readily produced by preparing an aqueous solution comprising the heterologous protein (such as IL-7) and the amphiphilic β-hairpin peptides as disclosed herein (such as AcVES3) and altering one or more characteristics of the solution, wherein a hydrogel is formed. As discussed above, the characteristic altered may be any characteristic that results in formation of a hydrogel upon its alteration, such as ionic strength, temperature, concentration of a specific ion, and pH. In some embodiments, the hydrogel including the heterologous protein can be formed in a container (such as a syringe), for example a closed container.

The peptide hydrogel including an encapsulated protein can be used for any suitable purpose. For example, peptide hydrogels with an encapsulated therapeutic protein can be administered to a subject in need thereof (for example, by injection to a target location in the subject). T cells are essential for the immune response to opportunistic infections, yet are deficient in subjects with HIV/AIDs, sepsis, and also in chemotherapy and bone marrow transplantation patients. Administration of Interleukin-7 (IL-7) is used to maintain and increase the number and function of endogenous T cells, as well as to enhance and promote the transfer of T cells, such as in CAR T cell therapy for cancer. Thus, the peptide hydrogel comprising dispersed IL-7 protein can be administered to a subject to provide IL-7 to maintain and promote endogenous T cell function, for example to treat or inhibit opportunistic infections, HIV/AIDs, and/or sepsis, as well as to enhance and promote T cell transfer procedures.

Peptide Hydrogels Including Heterologous Cells

In additional embodiments, the disclosed peptide hydrogel includes heterologous cells dispersed within the hydrogel, such as T cells, CAR T cells, and/or fibroblasts dispersed within the hydrogel. Peptide hydrogels for culture and delivery of cells are based on the amphiphilic β-hairpin peptides fused to an integrin binding peptide as disclosed herein.

Any appropriate amount of cells (e.g., CAR T cells) can be included in the hydrogel. For example, the hydrogel includes from $10^2$ to $10^6$ cells/mL dispersed within the hydrogel, such as from $10^3$ to $10^6$ cells/mL, from $10^4$ to $10^6$ cells/mL, from $10^5$ to $10^6$ cells/mL, from $10^2$ to $10^5$ cells/mL, from $10^2$ to $10^4$ cells/mL, from $10^2$ to $10^3$ cells/mL, from $10^3$ to $10^5$ cells/mL, from $10^3$ to $10^4$ cells/mL, or from $10^4$ to $10^5$ cells/mL dispersed within the hydrogel. In some embodiments, the hydrogel includes up to $10^6$ cells/mL dispersed within the hydrogel, such as up to $10^5$ cells/mL, up to $10^4$ cells/mL, or up to $10^3$ cells/mL dispersed within the hydrogel.

Peptide hydrogels including a heterologous cell can be readily produced by preparing an aqueous solution comprising the heterologous cell and the amphiphilic β-hairpin peptides as disclosed herein (such as AcVES3-RGDV) and altering one or more characteristics of the solution, wherein a hydrogel is formed. As discussed above, the characteristic altered may be any characteristic that results in formation of a hydrogel upon its alteration, such as ionic strength, temperature, concentration of a specific ion, and pH. In some embodiments, the hydrogel including the heterologous cell can be formed in a container (such as a syringe), for example a closed container.

The peptide hydrogel including an encapsulated cell can be used for any suitable purpose. For example, peptide hydrogels with an encapsulated therapeutic cell can be administered to a subject in need thereof (for example, by injection to a target location in the subject). In the situation of cell delivery into humans, it is preferable to use chemically defined media devoid of any foreign animal-derived materials such as fetal bovine serum (FBS). Accordingly, for a peptide hydrogel preparation containing dispersed cells intended for administration to a human, the peptide hydrogel and cells are typically incubated in media devoid of any foreign animal-derived materials such as FBS, for example, the culture media can be Essential 8 Medium. In some embodiments, the at least 10% of the mammalian cells dispersed within a peptide hydrogel administered to a target location in a subject remain at the target location for at least 30 days after administration.

EXAMPLES

The following examples are provided to illustrate particular features of certain embodiments, but the scope of the claims should not be limited to those features exemplified.

Example 1

Design of a β-Hairpin Peptide Hydrogel for 3D Cell Culture and In Vivo Cell Delivery Development of three-dimensional (3D) cell culture matrices for tissue engineering is an important issue. Use of an injectable material is desirable for the 3D cell culture systems particularly for cell transplantation.

This example illustrated design, production, and assessment of a novel β-hairpin peptide hydrogel system to support 3D cell culture and in vivo cell delivery. An integrin-binding β-hairpin peptide is disclosed, AcVES3-RGDV, which forms a clear and rigid peptide hydrogel under physiological conditions. Two-dimensional (2D) and three-dimensional (3D) cell culture experiments using the peptide hydrogel were performed to evaluate its cyto-compatibility and cell proliferation. Moreover, in vivo cell delivery was performed using the peptide hydrogel and retention of the cells was monitored over a month.

The results demonstrate that the combination of a newly designed anionic self-assembling peptide hydrogel with an integrin-binding sequence motif creates a potent biomaterial for 2D and 3D cell culture and subsequent in vivo cell delivery. Trigger-dependent gelation of the peptide allows homogeneous cell encapsulation and its integrin-binding activity provides proliferation of encapsulated anchorage-dependent cells, though the system also may be applicable to anchorage-independent cells. The expanded cells can be directly delivered with the hydrogel to the target tissue site by syringe injection due to the shear-thinning recovery property of the hydrogel, and the delivered cells can be retained in the target tissue over an extended period of time. In summary, the 3D cell culture and cell delivery system using the integrin-binding peptide hydrogel have the potential for clinical use.

Design of an Integrin-Binding β-Hairpin Peptide Hydrogel

A series of anionic peptides was developed that minimize potential electrostatic interactions between the hydrogel and cells, but allow the cells to bind specifically to the hydrogel matrix for proliferation (FIG. 2A). These peptides were designed with two β-strands consisting of alternating hydrophobic valine residues and hydrophilic residues of glutamates or serines. The β-strands were connected by a four residue type II' turn, V$^D$PPT, which contained a D-Pro to lock the β-turn in place (the other residues were L-amino acids). The N-termini of the peptides were acetylated to remove potential positive charge effects. The net charges of the peptides were adjusted by number of glutamates and serines to enable the peptides fold under physiological conditions.

One of the peptides, AcVES3 was used as a starting template to develop an integrin binding peptide for 3D cell growth (FIG. 2B). To add cell adhesiveness, AcVES3-RGDV was designed with an integrin-binding 'RGDV' sequence motif at C-terminus separated with a four-residue glycine linker from the parent peptide sequence (see Hirano et al., Synthesis and cell attachment activity of bioactive oligopeptides: RGD, RGDS, RGDV, and RGDT. J Biomed Mater Res 25, 1523-1534 (1991)). AcVES3-RGEV peptide, which has a glutamic acid at the aspartic acid position of RGDV, was used as a non-integrin-binding control. At pH 7.4, all peptides should have a net charge of −5. CD measurement of AcVES3 demonstrated random coil in water, but in physiological buffer, there was β-sheet structure from the increased negative ellipticity peak centered around 216 nm (FIG. 3A). Similarly to AcVES3, AcVES3-RGDV and AcVES3-RGEV showed β-sheet structure formation only under physiological conditions versus water alone as well as AcVES3. The β-sheet formation of these three peptides was temperature dependent, with 37° C. achieving maximum β-sheet structure (FIG. 3B).

Figure 4:
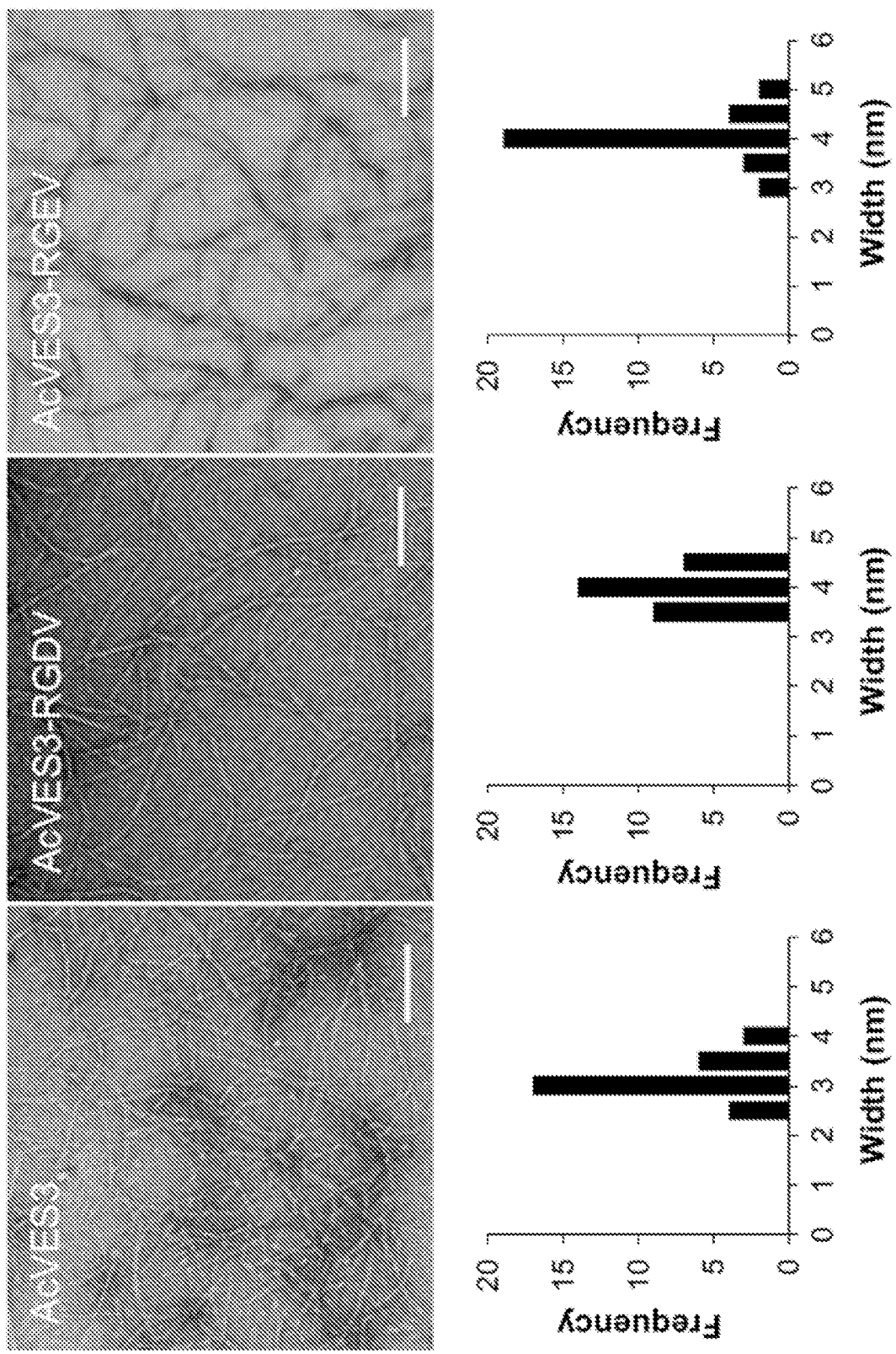

The nanoscale structure was assessed using TEM analysis (FIG. 4). The average of AcVES3 fibril width was 3.1±0.4 nm, which is similar to that of previously reported cationic β-hairpin peptides (~3 nm) (see Ozbas et al., Semiflexible chain networks formed via self-assembly of beta-hairpin molecules. Phys Rev Lett 93, 268106 (2004); Haines-Butterick et al., Controlling hydrogelation kinetics by peptide design for three-dimensional encapsulation and injectable delivery of cells. Proc Natl Acad Sci USA 104, 7791-7796 (2007)), indicating AcVES3 undergoes folding and fibril formation in a same manner as the cationic peptides. Fibrils of AcVES3-RGDV and AcVES3-RGEV displayed the same average width (4.0±0.4 nm) and they were slightly thicker (~1 nm) compared to AcVES3 fibrils. This increased fibril thickness of the two peptides is presumably due to the extended eight residues. Thus, these anionic peptides demonstrate β-sheet and fibril structures similar to previously designed cationic β-sheet hydrogels.

The mechanical properties of the three peptide hydrogels were further ascertained using rheology (FIGS. 5A-5D). These peptides undergo gelation in physiological buffer and cell culture media (DMEM), and have shear-thinning recovery properties similar to previously reported cationic β-hairpin peptide hydrogel (see Haines-Butterick et al., Controlling hydrogelation kinetics by peptide design for three-dimensional encapsulation and injectable delivery of cells. Proc Natl Acad Sci USA 104, 7791-7796 (2007)). This shear-thinning recovery property potentially enables them to be used as a syringe-deliverable cell vehicle (see Yan et al. Injectable solid hydrogel: mechanism of shear-thinning and immediate recovery of injectable beta-hairpin peptide hydrogels. Soft Matter 6, 5143-5156 (2010); Yan et al. Injectable solid peptide hydrogel as a cell carrier: effects of shear flow on hydrogels and cell payload. Langmuir 28, 6076-6087 (2012)). Though the peptide hydrogel exhibited lower storage modulus when DMEM was used as a trigger for gelation, the gels were still more rigid than bovine type I collagen gels by ~5-fold. Bovine type I collagen gels are approved by FDA and widely used as a matrix for 2D and 3D cell culture (see Hunt & Grover. Cell encapsulation using biopolymer gels for regenerative medicine. Biotechnol Lett 32, 733-742 (2010); Kanta. Collagen matrix as a tool in studying fibroblastic cell behavior. Cell Adh Migr 9, 308-316 (2015)), indicating that the peptide gels possess sufficient mechanical strength to support cells in a 2D and 3D cell culture environment.

Figure 5A:
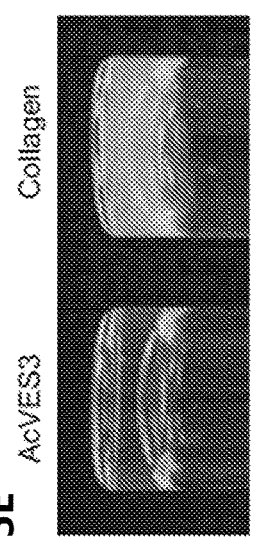
Figure 5B:
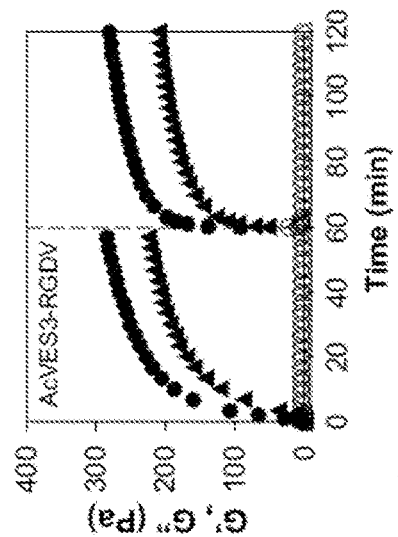
Figure 5E:
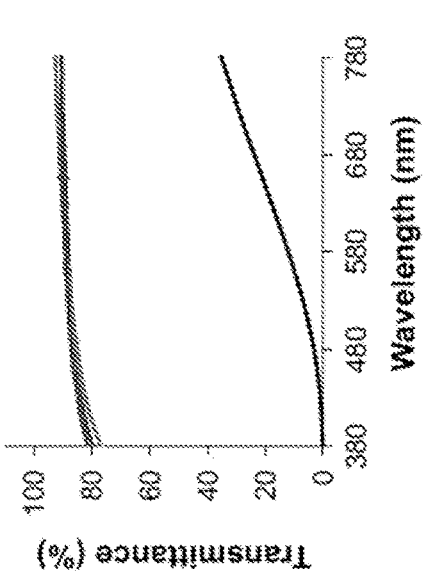
Figure 5C:
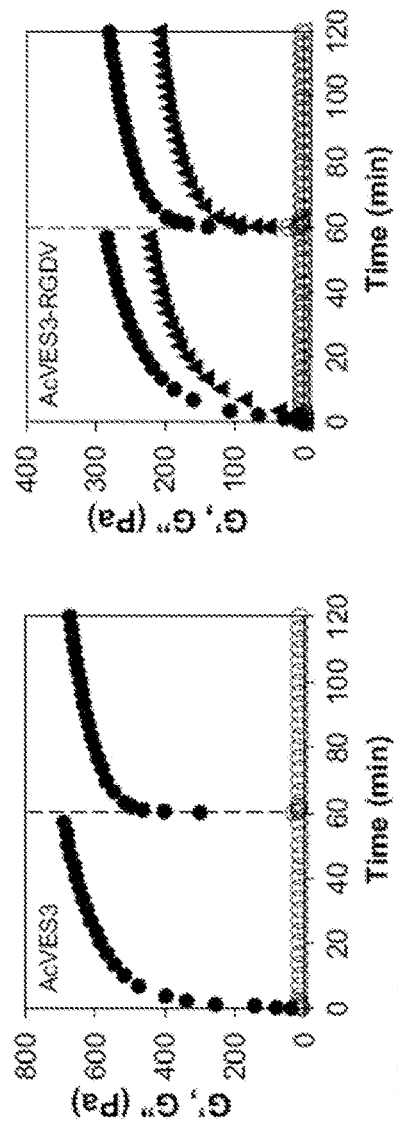
Figure 5D:
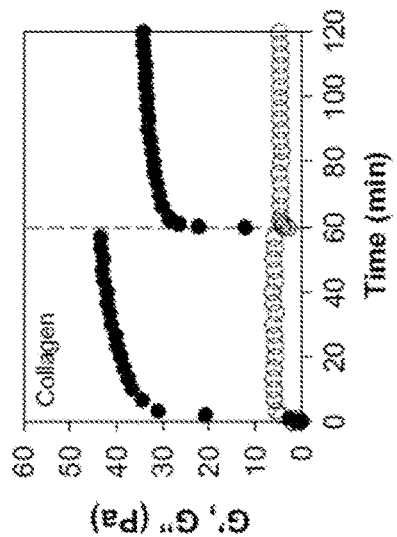
Figure 5F:
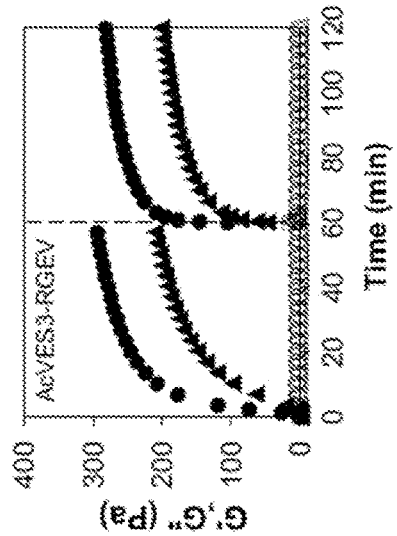

Transparency of 3D cell culture matrices needs to be considered from the aspect of optical observation (Tam et al. Transparent Porous Polysaccharide Cryogels Provide Biochemically Defined, Biomimetic Matrices for Tunable 3D Cell Culture. Chemistry of Materials 28, 3762-3770 (2016)). As shown in FIG. 5E, the peptides form transparent gels though the collagen forms a cloudy gel. To evaluate gel transparency, visible light transmittance in the range of 380-780 nm was measured (FIG. 5F). The peptide gels showed 80% transmittance at 380 nm and 90% at 780 nm, but the collagen gel showed 0% at 380 nm and 35% at 780 nm. This high transparency is also one of the excellent features of the peptide gel, that makes it easy to observe cells in the 2D and 3D cell culture experiments.

2D Cell Culture on Peptide Gel Surfaces in Serum-Free Cell Growth Media

Figure 9B:
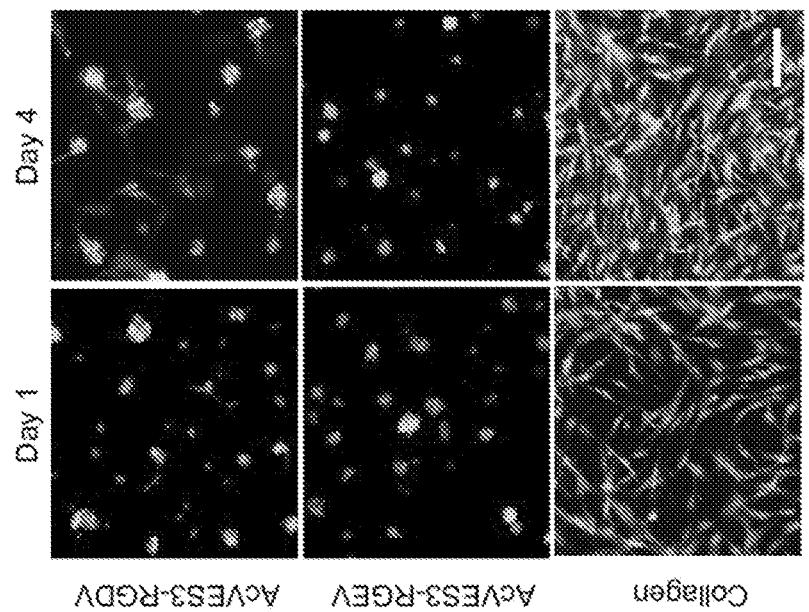
Figure 9A:
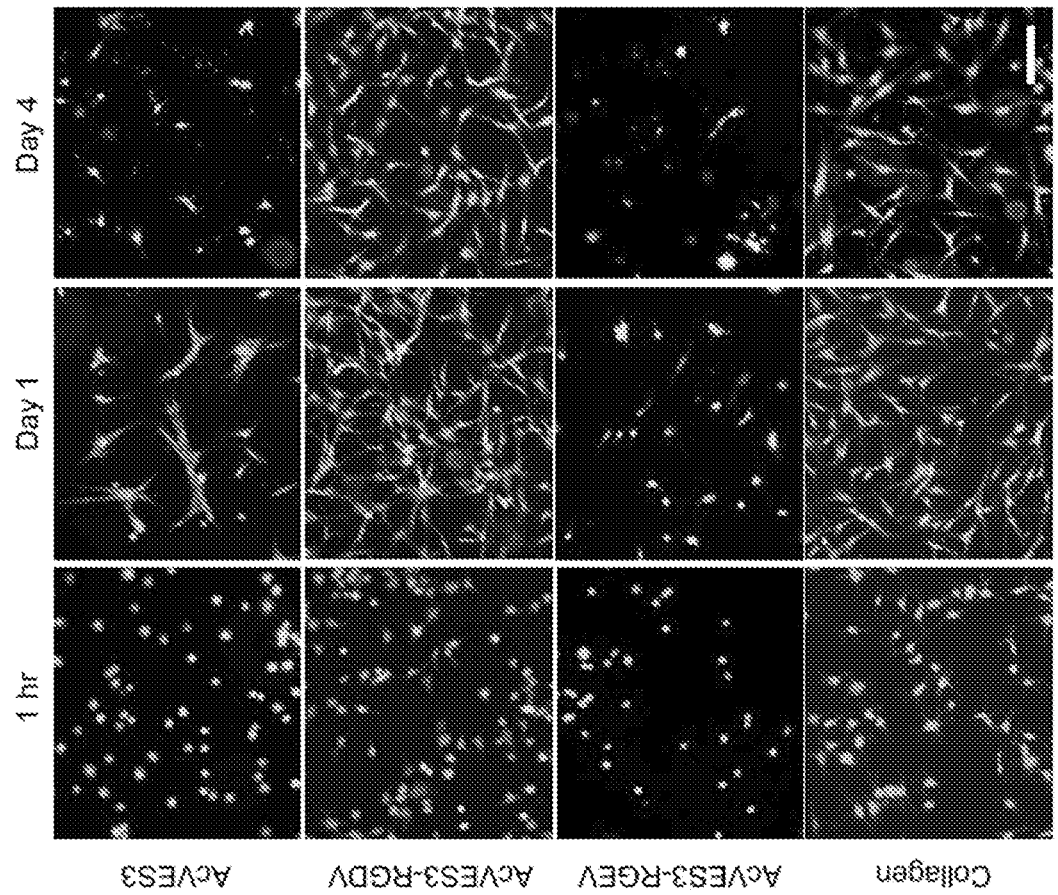

To evaluate cell adhesiveness of the peptide gels in 2D cell culture, HDFs (human dermal fibroblasts) were seeded onto surfaces of gels and cultured with either Essential 8 Medium or serum-free DMEM (FIG. 6A and FIG. 9A). Initially the cells adhered on AcVES3 gels for up to 1 day, but most of the cells detached by day 4. Since AcVES3 does not contain the 'RGD' cell adhesive factor, the gel surface was not compatible keeping cells attached for an extended duration. On the other hand, the majority of cells strongly attached and spread across the AcVES3-RGDV gels at day 1, and even after by day 4 they remained adherent and viable. The behavior of the cells on AcVES3-RGDV gels were generally similar to type I collagen gels. The control AcVES3-RGEV gels showed similar behavior to that seen with AcVES3 gels. Also tested was the cell adhesion of peptide gels using 10% fatal bovine serum (FBS)-supplemented DMEM media (FIG. 9B). In this case, all cells formed spherical aggregates on the peptide gels, indicating that serum proteins interfere with the interaction between cells and peptide fibrils. In the situation of cell delivery into humans, it is preferable to use chemically defined media devoid of any foreign animal-derived materials such as FBS (see Oikonomopoulos et al. Optimization of human mesenchymal stem cell manufacturing: the effects of animal/xeno-free media. Sci Rep 5, 16570 (2015)). Keeping this in mind, Essential 8 Medium was used, which is a chemically-defined medium specially formulated for the growth of human pluripotent stem cells, to evaluated cell proliferation profiles of the peptide gels (FIG. 6B). HDFs on AcVES3-RGDV gels proliferated to a similar degree as cells on collagen gels. The cells on the control AcVES3-RGEV gels were viable at day 4, but cell proliferation was not observed. Moreover, the AcVES3-RGDV gels promoted organization of actin stress fibers and focal contacts, indicating integrin signaling from the peptide gel surface allowing for cell adhesion and spreading in a similar manner as seen with the collagen gels (FIG. 6C). These 2D cell culture experiments demonstrated that integrin-mediated interactions between cells and the gel surface was crucial for not only cell adhesion, but also for cell proliferation, and all of this was influenced by media composition. Taken together, these results indicate that the AcVES3-RGDV gels are suitable for expansion of anchorage-dependent cells, such as fibroblasts.

3D Cell Encapsulation Culture in Peptide Gels with Serum-Free Growth Media

Figure 7C:
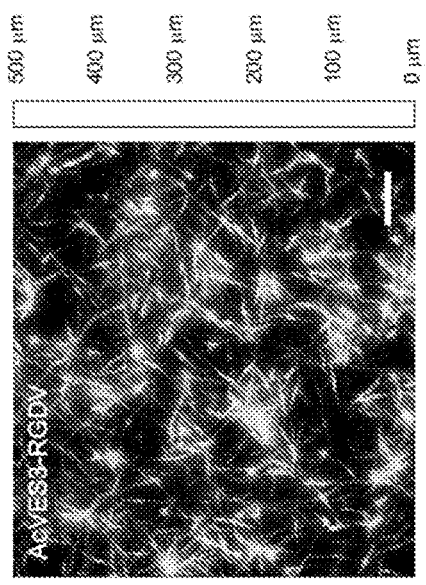
Figure 7D:
Figure 7E:
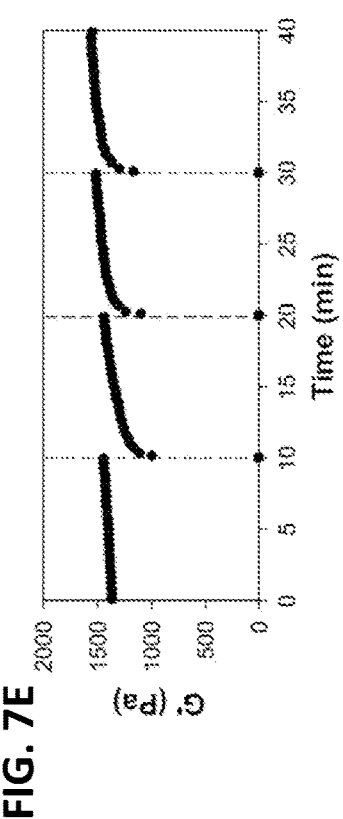
Figure 7A:
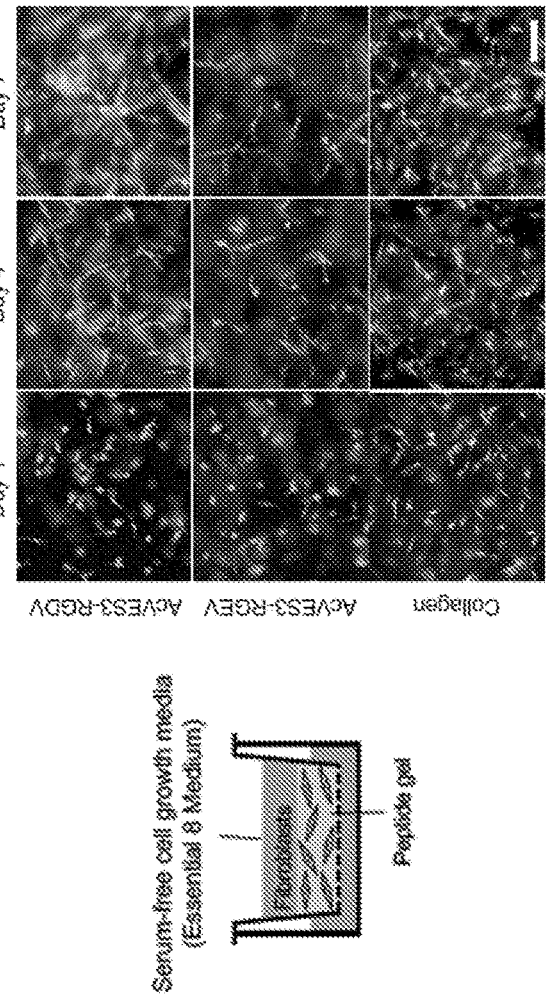
Figure 7B:
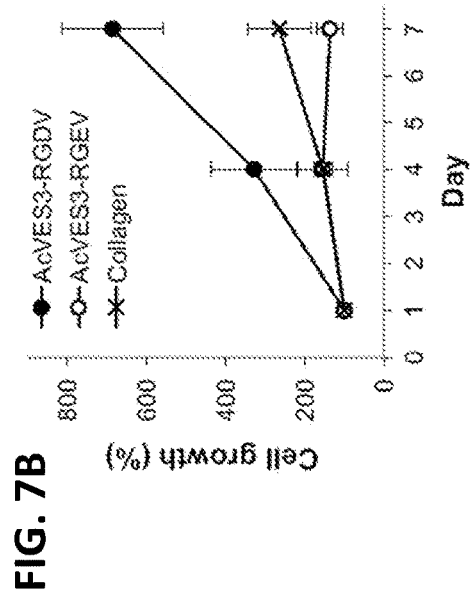

HDFs were encapsulated and cultured in hydrogels with Essential 8 Medium to assess their performance in 3D culturing. In the AcVES3-RGDV gels, these cells proliferated well with minimal cell death even after one week of culturing (FIG. 7A). HDFs in the control AcVES3-RGEV gels were viable at day 7 but did not proliferate, which was consistent with the 2D cell culture results. These data suggest the peptide gels were not cytotoxic in 3D culture platform and cell proliferation was dependent on cell adhesiveness of the matrix. The cell proliferation rate in the AcVES3-RGDV gels was 2-3-fold faster than the collagen gel (FIG. 7B). FIG. 7C shows the distribution of encapsulated cells at the different surface heights (0-500 μm) for the AcVES3-RGDV gels on day 4. These cells were homogenously distributed throughout the gel matrix, and interestingly, every cell visualized displayed three-dimensional extended morphology with actin cytoskeleton organization in a similar manner as was observed for cells in collagen gels (FIG. 7D). Several groups have reported cell encapsulation and 3D culturing using synthetic hydrogels, including self-assembling peptide gels (See Haines-Butterick et al., Controlling hydrogelation kinetics by peptide design for three-dimensional encapsulation and injectable delivery of cells. Proc Natl Acad Sci USA 104, 7791-7796 (2007); Jacob et al. Self-healing hydrogels composed of amyloid nano fibrils for cell culture and stem cell differentiation. *Biomaterials* 54, 97-105 (2015)). However, prior to this disclosure, the strong adhesion and proliferation of encapsulated cells in injectable gels was not possible. The cell behaviors in the AcVES3-RGDV gels indicate that the gel has not only enough rigidity to support cells, but also flexibility to allow cells to elongate by remodeling of the gel networks. The results demonstrate that the AcVES3-RGDV peptide gel is an ideal 3D cell culture matrix, which has comparable biological and mechanical properties as seen with ECM (extracellular matrix)-derived protein hydrogels. Finally, AcVES3-RGDV gels retained their shear-thinning recovery property after cell encapsulation and culture for 4 days (FIG. 7E). The storage moduli of the gels were constant even after multiple physical disruptions. Taken together, these results highlight that the peptide matrix can be syringe-based injectable after 3D cell expansion and were tested in the next section.

Hydrogel-Based Cell Delivery In Vivo

Murine animal experiments were performed to evaluate in vivo effects of peptide gels for cell delivery. Red fluorescent protein (RFP)-expressing fibroblasts were utilized to detect and follow delivered cells by fluorescence imaging. When the cell suspension control was injected into mice, these cells disappeared after one week, which may be a consequence of either cell dispersion and/or apoptosis (FIGS. 8A and 8B). On the other hand, when the peptide gel was used as a vehicle, dissipation of the injected cells was significantly slower by 6-fold (calculate approximately from the slopes of the lines) and cells were retained for over 40 days after initial injection. This dissipation of cells might be dependent on cell death and/or degradation of the gels. At day 42, approximately 2% of the RFP signal was still detected at the RFP-HDFs/AcVES3-RGDV gel injection site. At this time, target subcutaneous tissue was directly observed after dissection of the murine skin. Examination of the tissue revealed no apparent inflammation around the injection site and complete absence of any peptide gel, but RFP-HDFs were observed on the surface of the subcutaneous tissue, indicating that the cells eventually engrafted onto the tissue after degradation of the peptide gel (FIG. 8C). To confirm engraftment, RFP-positive tissue was scraped and dispersed with a cell strainer and found that these cells contained RFP-positive HDFs and mouse-derived RFP-negative cells. In vitro culture of these cells demonstrated that the RFP-positive cells were able to adhere and proliferate under serum-supplemented conditions (FIG. 8D). These results suggest that AcVES3-RGDV gels dramatically enhance localization and retention of the delivered cells and also support engraftment.

In light of the above, hydrogels formed from the AcVES-RGDV peptide are cytocompatible even in the absence of serum. This is surprising because prior peptide-based hydrogels typically require serum to be present to ensure cytocompatibility; proteins from the serum coat the matrix of these gels, which provides a protective layer between the peptide matrix and the cells. Because of this, the prior peptide-based hydrogels are not chemically defined in that the composition of the serum protein coatings is not known, and therefore, such peptide hydrogels may not be preferred for in vivo implantation of cell-based therapeutics. In contrast, the unique charge state and hydrophilicity of the fibrils formed by the AcVES3-RGDV peptide is believed to provide the cytocompatible properties of corresponding hydrogel. No serum proteins are needed to coat and passivate the surface of the hydrogels formed by the disclosed peptides (such as Ac-VES3 and AcVES3-RGDV), and thus the gel is chemically defined. In addition to providing superior cytocompatibility, hydrogels formed from AcVES3-RGDV were biocompatible, display shear-thin/recovery mechanical properties (allowing the gel to be delivered locally by simple syringe injection) and retain dispersed cells even after injection to a target location in an animal. Taken together, the cytocompatible, biocompatible, and mechanical properties of the disclosed hydrogels make them ideal for therapeutic cell delivery.

Methods

Peptide synthesis and purification. Peptides were synthesized on PL-rink resin (Agilent Technologies) using an automated ABI 433A peptide synthesizer (Applied Biosystems). Syntheses were performed via solid-phase Fmoc-based chemistry with 1H-benzotriazolium-1-[bis(dimethylamino)methylene]-5-chloro-hexafluorophosphate-(1-),3-oxide (HCTU, Peptide International) activation. Fmoc-protected amino acids were purchased from Novabiochem. Dried resin-bound peptides were cleaved from the resin and side-chain deprotected with a TFA/thioanisole/ethanedithiol/anisole (90:5:3:2) cocktail for 2 h under an argon atmosphere. Crude peptides were precipitated with cold ethyl ether and lyophilized. Peptides were purified by reversed phase-high performance liquid chromatography (RP-HPLC) with a Phenomenex PolymerX column employing a linear gradient from 0-80% acetonitrile with 20 mM ammonium bicarbonate, peptide peaks fractionated, and finally lyophilized. Peptides were converted to sodium salts by the addition of 20 mM ammonium bicarbonate at 1 mg mL$^{-1}$ and a NaOH solution added and subsequently lyophilized until use. Analytical HPLC and electron spray ionization (negative mode) mass spectrometry confirmed the purity and composition of the peptides.

Circular dichroism (CD). CD spectroscopy of the peptides was measured on an Aviv 410 spectropolarimeter (Aviv Biomedical). A 300 μM solution of peptide was prepared and an equal volume of buffer (50 mM HEPES containing 300 mM NaCl, pH 7.4) was added. A peptide solution was quickly transferred to 1 mm path length cell previously equilibrated at 5° C. Then, CD wavelength spectra were collected from 200-260 nm at 37° C. CD spectra were also collected as a function of temperature to follow β-sheet formation at 216 nm (2-52° C. with a 5° C. increment and a 10 min equilibration time for each temperature point. The mean residue ellipticity [θ] was calculated from [θ]=(θ$_{obs}$/10lcr), where θ$_{obs}$ is the measured ellipticity in millidegree, l is the cell path length in centimeters, c is the concentration in molar, and r is the number of residues of peptide sequence.

Transmission electron microscopy (TEM) analysis. The hydrogel nanostructure of the peptide gels was observed using a Hitachi H-7650 transmission electron microscope at a voltage of 80 kV. A 1 wt % solution of peptide and an equal volume of buffer (50 mM HEPES containing 300 mM NaCl, pH 7.4) was mixed and incubated overnight at 37° C. to allow for gelation. The next day, samples for TEM analysis were prepared by suspending 5 μL of the resulting peptide gel in 195 μL of water to yield a 40-fold dilution. Small amounts (5 μL) of each diluted gel solution were applied to separate carbon coated copper grids. After 1 min, the grid was washed with water. Then, a 1 w/v % uranyl acetate aqueous solution was placed on each grid for negative staining. Excess staining solution was blotted away, left to air dry, and the grids were imaged immediately.

Oscillatory rheology. Rheology experiments were performed on an AR-G2 rheometer (TA Instruments) equipped with a 25-mm stainless steel parallel plate geometry with a 0.5 mm gap height. To mimic syringe delivery, a shear-thinning recovery procedure was used. A 1 wt % peptide solution in water was prepared on ice and an equal volume of buffer (50 mM HEPES containing 300 mM NaCl, pH 7.4) was added to initiate gelation. For the gelation by DMEM, a 1 wt % peptide in 285 mM sucrose was prepared and an equal volume of HEPES-supplemented DMEM was added. A 300 μL of the solution was immediately transferred to the rheometer plate equilibrated at 5° C. Oil was placed around the sample and on the plate to prevent evaporation. After the temperature was ramped to 37° C. (0.5° C. s$^{-1}$), a 1-hour dynamic time sweep was performed to monitor the storage (G') and loss (G") modulus of the resulting hydrogel. An angular frequency of 6 rad s$^{-1}$ and 0.2% strain was applied. After which, a 1000% strain was applied for 30 s to disrupt the material. Subsequently, the ability of the hydrogel to reheal itself was monitored by measuring the recovery of G' at 6 rad s$^{-1}$ and 0.2% strain for additional 1 hour. Bovine type I collagen gels (0.3 wt %, Thermo Fisher Scientific) were prepared following manufacturer's instructions.

Rheology measurements of cell-encapsulating gels after 4 days of 3D cell culturing were performed using 8-mm stainless steel parallel plate geometry with a 0.5 mm gap height. A cell-encapsulating gel (100 μL) in a transwell insert (for 24 well plates, Corning) was transferred to the rheometer plate previously equilibrated at 37° C. and oil was placed around the sample. Dynamic time sweep was performed with 6 rad s$^{-1}$ angular frequency and 0.2% strain, the gel was shear-thinned at 1000% strain for 30 s every 10 min, and allowed to recover by reducing the strain to 0.2%.

Optical transmittance measurements. Optical transmittance measurements were performed using Agilent 8453 UV-visible Spectroscopy System. A 1 wt % aqueous solution of peptide was prepared and an equal volume of buffer (50 mM HEPES containing 300 mM NaCl, pH 7.4) was added to initiate gelation. A 150 μL of the solution was immediately transferred to a 10 mm path length quartz cell and incubated for 1 hour at 37° C. to complete gelation. A 0.3 wt % collagen gel was also prepared following manufacturer's instructions. The transmittance of the gels was measured in the wavelength range of 380-780 nm.

Cell culture. Human neonatal dermal fibroblasts (HDFs) and red fluorescent protein (RFP)-expressing human neonatal dermal fibroblasts (RFP-HDFs) were purchased from Cell Applications and ANGIO-PROTEOMIE™, respectively. Cells were maintained in Dulbecco's Modified Eagle Medium (DMEM, low glucose, Thermo Fisher Scientific) containing 10% FBS, 100 U/mL penicillin, and 100 μg/mL streptomycin.

2D cell culture on peptide gels. Peptides were initially dissolved in water at 1 wt % on ice and mixed with an equal volume of ice-cold 2×HEPES buffer (50 mM HEPES, 300 mM NaCl, pH 7.4). The peptide solution (50 μL per well) was transferred to a non-tissue culture treated 96-well plates and incubated at 37° C. to initiate gelation. After 1 hour, HDFs (2×10$^4$ cells per 200 μL, per well) in serum-free DMEM, 10% FBS supplemented DMEM, or Essential 8 Medium (Thermo Fisher Scientific) were seeded on the peptide gels and cultured for 4 days. Bovine type I collagen gels (0.3 wt %, 50 μL per well) were prepared in 96-well plates following manufacturer's instructions.

3D cell culture in peptide gels. Peptides were initially dissolved in 285 mM sucrose at 1 wt % on ice and mixed with an equal volume of cell suspension in serum-free HEPES-supplemented DMEM (2×10$^6$ cells mL$^{-1}$). The cell-peptide suspension (5×10$^4$ cells per 50 μL per insert) was transferred to a Falcon cell culture insert (for 24-well plates, 8 μm pore size, Corning) and incubated at 37° C. for 30 min for gelation. These inserts were previously coated with the empty hydrogel (30 μL per insert) to avoid cell adhesion to the bottom surface of the inserts. After gelation of cell-peptide solution, 500 μL of Essential 8 Medium were added to the top and bottom of the gels. Type I collagen gels were prepared following manufacturer's instructions. Briefly, a 0.4 wt % collagen solution was prepared on ice and mixed with cell suspension in serum-free DMEM (4×10$^6$ cells mL$^{-1}$) at a ratio of 3:1 (0.3 wt % collagen, 1×10$^6$ cells mL$^{-1}$).

Cell viability assay. Cell viability was evaluated by live and dead cell staining after 2D and 3D cell culture. Serum-free DMEM containing 1 μM calcein-AM and 2 μM ethidium homodimer-1 was added to the cells (200 μL per well for 2D culture and 500 μL each to the top and bottom of the gels for 3D culture). After incubation at 37° C. for 30 min, live and dead cells were visualized using EVOS FL Auto Cell Imaging System (Thermo Fisher Scientific). For the pseudo-colored composite image of varying heights of encapsulated cells, images of the live-stained cells were captured every 5 μm of height. Then Z-stack images for each 100 μm were flattened using the EVOS software, and the flattened images were pseudo-colored and merged using ImageJ.

Cell proliferation assay. A cell proliferation assay was performed using Cell Counting Kit-8 (CCK-8, Dojindo Molecular Technologies) for 2D and 3D cell culture. Serum-free DMEM containing 10% CCK-8 was added to the gels (200 μL per well for 2D culture; 500 μL to the top of the gels for 3D culture) and incubated for 2 hours at 37° C. Subsequently, media were transferred to 96-well plates (150 μL per well) and their absorbance measured at 450 nm relative to control viabilities from day 0 for 2D cell culture and day 1 for 3D cell culture. Experiments were performed in triplicate.

Cytoskeleton staining. For 2D cell culture, the peptide and collagen gels (70 μL) were prepared as described above on the glass bottom of 35 mm dishes (7 mm glass diameter, MatTek). HDFs in Essential 8 Medium ($1.5 \times 10^5$ cells per 3 mL) were added to the dishes and incubated at 37° C. for 24 hours. Cells were fixed and permeabilized with 4% paraformaldehyde and 0.1% Triton X-100 in PBS for 15 min, and then blocked with 1% BSA in PBS. Cells were incubated with anti-vinculin antibody (hVIN-1, Sigma) for 1 hour at room temperature. Then, a goat anti-mouse IgG (H+L) cross-adsorbed secondary antibody, Rhodamine Red-X (2 µg mL$^{-1}$, Thermo Fisher Scientific), Alexa Fluor 488 phalloidin (5 units mL$^{-1}$, Thermo Fisher Scientific), and Hoechst 33342 (5 µg mL$^{-1}$, Invitrogen) in PBS were added to the dishes and incubated for 1 hour at room temperature. After washing, cells were visualized using an EVOS FL Auto Cell Imaging System.

For 3D cell culture, HDF-encapsulating gels were prepared in the Falcon cell culture inserts ($5 \times 10^4$ cells per 50 µL gel per insert) as described above. Next, cells were cultured in Essential 8 Medium for 4 days. Cells were then fixed, permeabilized, and stained simultaneously with 4% paraformaldehyde, 0.1% Triton X-100, and Alexa Fluor 488 phalloidin (5 units mL$^{-1}$) in PBS (500 µL to the top and bottom of the gels) for 1 hour at room temperature. After washing with PBS (15 min for 3 times), Hoechst 33342 (5 µg mL$^{-1}$, 500 µL to the top and bottom of the gels) was added for 30 min at room temperature. Cells were washed with PBS and visualized using an EVOS FL Auto Cell Imaging System.

In vivo studies. Six- to eight-week-old non-tumor bearing female athymic nude mice were used for this experiment (n=3). Animal care was in accordance with the procedures outlined in the Guide for Care and Use of Laboratory Animals (National Research Council, 1996; National Academy Press, Washington, D.C.) and animal protocols were approved by the Frederick National Laboratory for Cancer Research (FNLCR) Institutional Animal Care and Use Committee.

Hydrogel-based in vivo cell transplantation. RFP-HDFs were encapsulated in 0.5 wt % AcVES3-RGDV at $10^7$ cells mL$^{-1}$ as described in the 3D cell culture section. After gelation, the cell-peptide gel ($10^6$ cells per 100 µL) was injected into the left dorsal region of the mouse and as a control, RFP-HDF suspension in serum-free DMEM ($10^6$ cells per 100 µL) was injected into the right dorsal region of the mouse.

In vivo fluorescence imaging. Multispectral fluorescence imaging was performed daily (Monday-Friday) for 42 days using a Maestro Flex imager (PerkinElmer). Briefly, mice were anesthetized for 3-4 minutes in an induction chamber with 3% isoflurane with filtered air (0.2 µm filter) used as a carrier at a flow rate of 1 liter per minute. After isoflurane induction, the mice were transferred to an imaging chamber, where isoflurane was reduced to 2% and $O_2$ was used as a carrier. The imaging platform was kept at 37° C. to maintain the mouse's internal temperature. Image acquisition (Maestro software, ver. 2.10.0) of the RFP fluorescence signal utilized a 533±26 nm excitation filter (placed in front of the 300 W xenon excitation source), a 580 nm long-pass filter (placed in front of the CCD) and implementing a multispectral imaging acquisition of 550-720 nm range, 10 nm increment, auto exposure (typically 0.5-5 seconds per emission wavelength), with a 2×2 pixel binning, resulting in a stack of images (image cube). RFP signal was distinguished from the tissue autofluorescence by employing vendor specified unmixing protocol. Quantitative analysis was performed by drawing a standard circular region of interest (ROI) over the injection site of the unmixed RFP component image. The total RFP signal (scaled counts second$^{-1}$) within each ROI was measured and plotted as a function of time.

Collection of RFP-HDFs from the tissue graft. After in vivo imaging on day 42, mice were euthanized using $CO_2$ and ex vivo images (Maestro Software) were acquired by exposing the cell-peptide gel injection site. Image acquisition and processing were performed with the same parameters as performed for in vivo imaging as stated above. Utilizing the unmixed RFP image to guide resecting the RFP-positive tissue, the RFP positive cells were resected and then homogenized by squeezing them through a cell strainer. The collected cells were then cultured on a tissue culture plate with FBS-supplemented DMEM for 10 days and observed using an EVOS FL Auto Cell Imaging System.

Example 2

Tunable Protein Release from a Peptide Hydrogel

This example provides general and specific strategies for delivery of a protein of interest that can reliably control the rate of release from a peptide hydrogel using a designed electrostatic interaction between a peptide tag fused to the protein of interest and the hydrogel. The results illustrate a new strategy to control protein release from a peptide hydrogel. By altering the charge of the peptide tag incorporated onto the protein encapsulated in the hydrogel, mainly by changing the arginine content, a range of release profiles that were previously unattainable without alterations to the hydrogel material itself has been obtained. Furthermore, using the curves generated from different peptide tag lengths, the release profile of a linear combination of two tags to achieve a finely-tuned release timeline was could predicted and validated. The presence of heterologous protein (EGFP) and corresponding peptide tag did not alter the material properties of the hydrogel, as protein loaded AcVES3 hydrogel had identical stiffness and shear-thin recovery capabilities as the empty gel. It is anticipated that the approach provided herein will streamline protein delivery.

Protein therapeutics have become a significant source of new drugs in recent years due to high affinity and selectivity towards specific biological targets. However, proteins cannot be delivered orally and the need for constant IV injections can complicate treatment regimens and reduce patient compliance. Various delivery platforms have been investigated for improved protein delivery, but challenges remain. For many materials, the formulation process of encapsulating protein lacks precise control over the amount of drug loaded, and undesirable interactions between proteins and organic cosolvents, crosslinking agents, or the materials themselves can lead to denaturation (see, Ma, G. Journal of Controlled Release 2014, 193, 324-340). Additionally, it has been difficult to design and achieve sustained release of proteins over weeks or months (see, e.g., Vaishya et al., Expert Opinion on Drug Delivery, 12, 415-440, 2015).

Hydrogels, materials made from either synthetic or natural polymers, have received significant attention towards improving protein delivery. This is due to the fact that the soft, highly aqueous environment is compatible with protein encapsulation and many gels can be directly injected in to a site of interest. Unfortunately, there is currently no universal approach that can fine tune the release timeline of a specific protein other than altering the hydrogel itself (See Vulic et al., Biomacromolecules, 15: 3867-3880, 2014; Martino et al., PNAS, 110: 4563-4568, 2013; Vulic & Shoichet, J American Chemical Society, 134: 882-885, 2012; Battig et al., J American Chemical Society, 134: 12410-12413, 2012; Bertz et al., J Biotechnology, 163, 243-249, 2013; Freeman et al., Biomaterials, 29: 3260-3268, 2008; Young et al., J Controlled Release, 109: 256-274, 2005). Such alterations can drastically affect the material properties (i.e. rigidity and reheating), and the long regulatory process to approve different materials can be burdensome. What is needed is a simple method that can predictably control the rate of protein release, be genetically incorporated, and be readily translatable to different types of proteins without having to redesign the hydrogel for each delivery application.

Over the last decade, a variety of hydrogels based on self-assembling β-hairpin peptides have been developed. The triggering mechanism for gelation is dependent on the specific peptide, but the folding and self-assembling process results in fiber-containing nanostructures as observed by electron microscopy. The hydrogels also have self-healing properties, as they can respond to shear forces and rapidly recover their rigidity.

Figure 10:
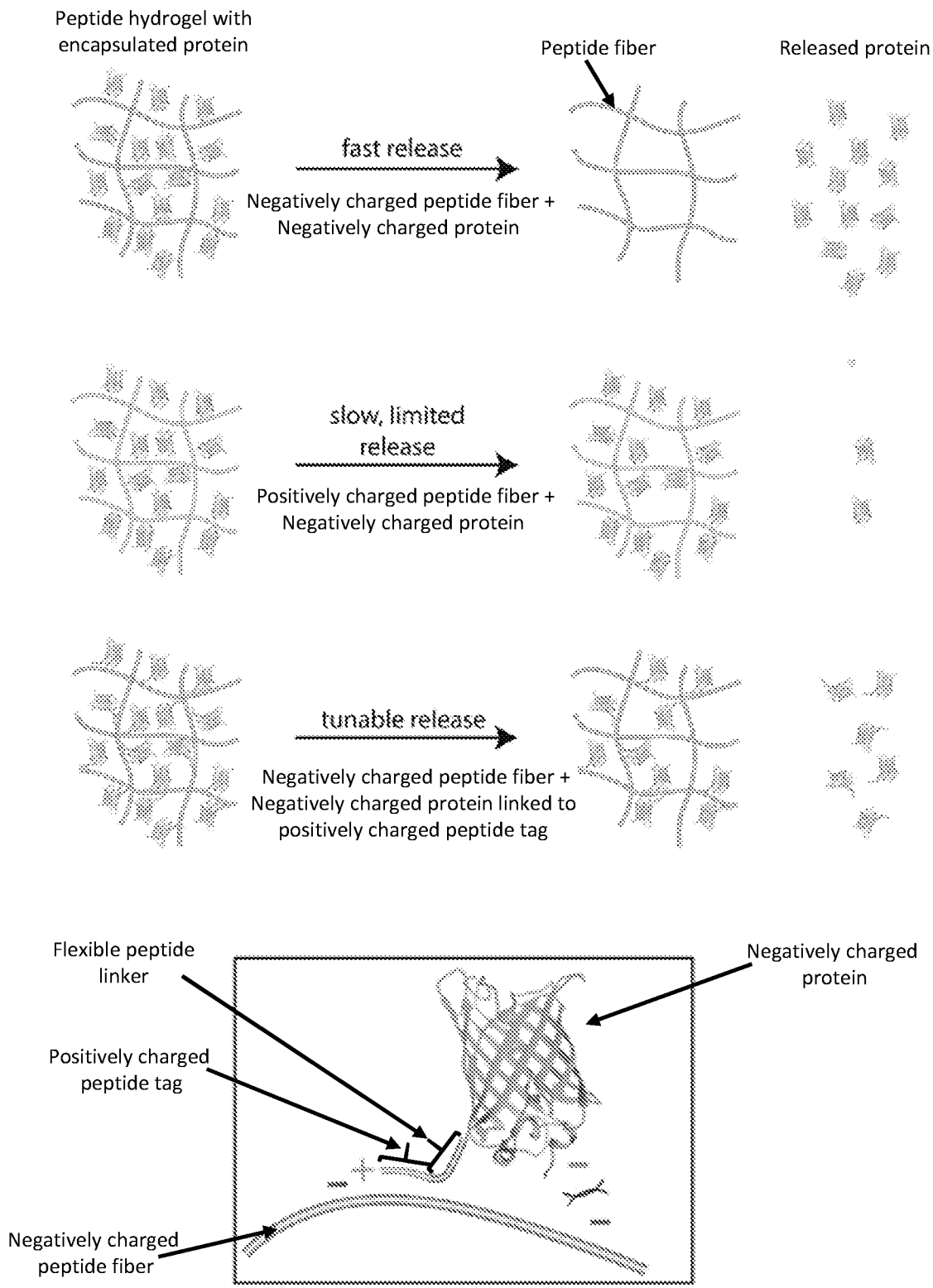

Initial protein delivery from peptide hydrogels was limited to rapid or very slow release by pairing a protein with a hydrogel of either the same or opposite charge, respectively (see Branco et al., Biomaterials, 31, 9527-9534, 2010; Nagy-Smith et al., J Materials Chemistry B, 4, 1999-2007, 2016). To access a more diverse range of release timelines, a new system was devised in which a genetically incorporated peptide tag on a protein of interest was engineered to interact with the hydrogel matrix (FIG. 10). The native protein region and the hydrogel are of the same net charge to eliminate adsorption interactions that could lead to denaturation, and the rate of release is controlled by adjusting the number of charges in the fusion tag.

Initially, the fluorescent protein EGFP and the hydrogelating peptide AcVES3 were selected, both having a net negative charge, and a cationic fusion tag was installed at the N-terminus of EGFP. AcVES3 was chosen because it forms strong gels at low weight percentages and is highly cytocompatible. EGFP is a good model because its high extinction coefficient allows for the detection of low protein concentrations by UV, while its folding and activity can be easily assessed by comparing the fluorescence properties of the protein before encapsulation and after release from the gel. After preliminary validation by comparing the release of EGFP and its N-terminal His-6 tagged precursor (NH6), a small library of proteins with cationic fusions of different lengths was designed and generated (see the following table). To sufficiently separate the fusion domain from the main chain of EGFP, a 10 amino acid peptide linker consisting of glycine and serine was also incorporated.

| Name | Protein [Peptide Tag]-[peptide linker]-[EGFP] | Basic A.A. in peptide tag | pI |
| --- | --- | --- | --- |
| EGFP | [EGFP] | — | 5.58 |
| NH6 | [MRSGSHHHHHHRSDITSLYKKVGIEGR]-[EGFP] | 3 Arg, 2 Lys | |
| RH1 | [G(RH)$_1$R), SEQ ID NO: 12]-[(GGSGS)$_2$, SEQ ID NO: 18]-[EGFP] | 2 Arg | 5.93 |
| RH2 | [G(RH)$_2$R), SEQ ID NO: 13]-[(GGSGS)$_2$, SEQ ID NO: 18]-[EGFP] | 3 Arg | 6.13 |
| RH3 | [G(RH)$_3$R), SEQ ID NO: 14]-[(GGSGS)$_2$, SEQ ID NO: 18]-[EGFP] | 4 Arg | 6.32 |
| RH4 | [G(RH)$_4$R), SEQ ID NO: 15]-[(GGSGS)$_2$, SEQ ID NO: 18]-[EGFP] | 5 Arg | 5.52 |
| RH5 | [G(RH)$_5$R), SEQ ID NO: 16]-[(GGSGS)$_2$, SEQ ID NO: 18]-[EGFP] | 6 Arg | 6.74 |
| RH6 | [G(RH)$_6$R), SEQ ID NO: 17]-[(GGSGS)$_2$, SEQ ID NO: 18]-[EGFP] | 7 Arg | 7.02 |

The net charge of AcVES3 is −5. The amino acid sequence of the EGFP protein used in these assays is as follows:

(SEQ ID NO: 19)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK

Figure 11A:
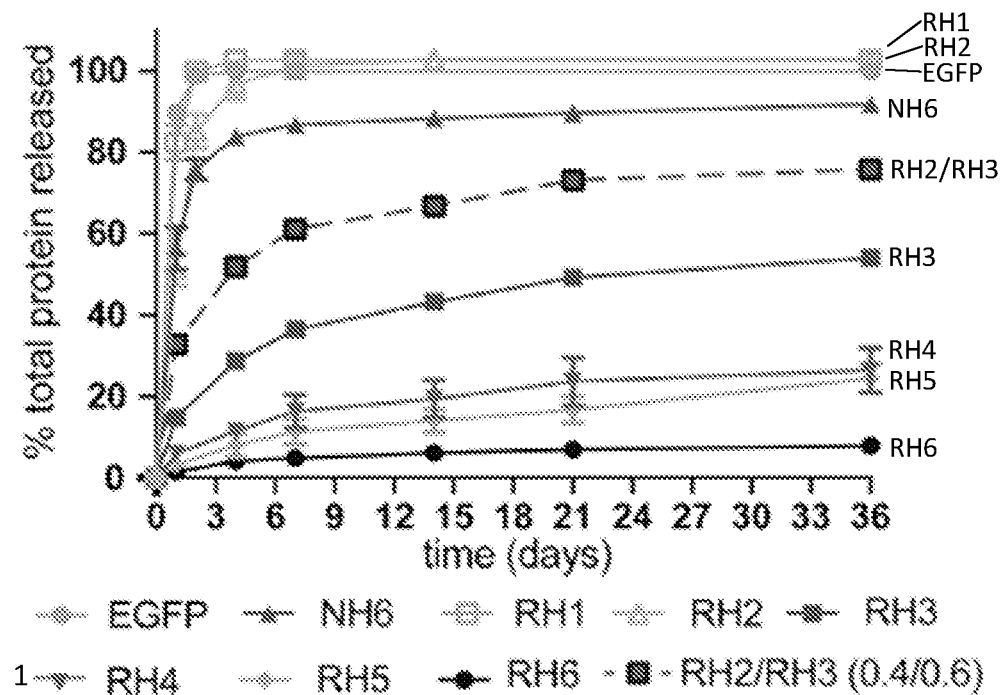
Figure 11B:
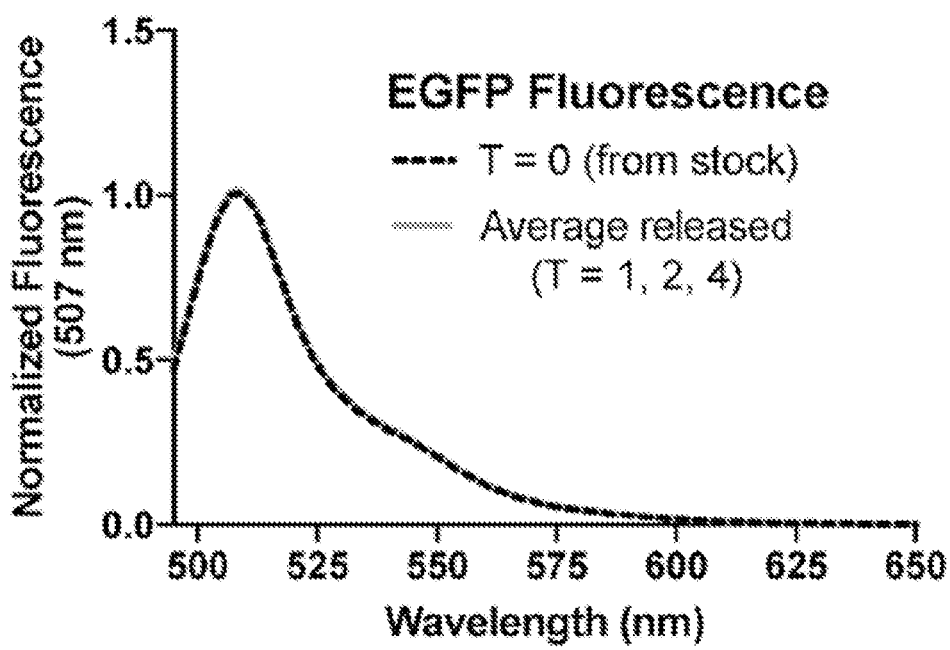

After encapsulation of the proteins in 0.5 wt % AcVES3 hydrogels, UV absorbance readings of the gel supernatants at various time points were used to determine the extent of protein release (FIG. 11A), and fluorescence spectra were taken to assess the activity (FIG. 11B). Visual examinations of each gel allowed for the crude assessment of active protein remaining inside the network when accounting for the amount released. As predicted, the longer fusion domains resulted in slower release of protein from the hydrogel compared to unmodified EGFP or the shorter fusions. The isoelectric point (pI) of a given protein was generally a good predictor of how well the fusions would be retained with respect to the first generation of designed analogs. However, although NH6 and RH3 have similar isoelectric points, the latter had a significantly slower release rate (FIG. 11A). NH6 contains a variety of amino acid functionalities (charged, polar, nonpolar) and a more diffuse distribution of basic residues in its fusion domain. It is important to note that all fusion proteins retained their fluorescence, indicating that long-term encapsulation did not alter functional viability (FIG. 112B).

Figure 11C:
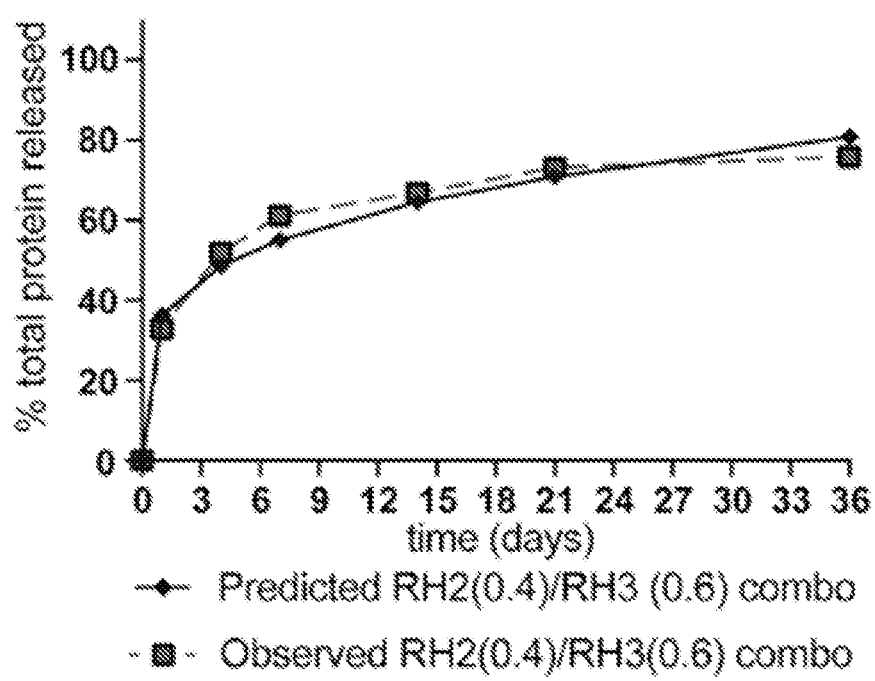

Combinations of different fusions were sought to access additional time regimes and achieve further control over protein release. To assist in the formulation process, the release data for individual EGFP analogs (FIG. 11A) were fit to a Korsmeyer-Peppas function using nonlinear regression and combinations could be generated based on a desired release curve. The predicted release rate of a mixture of 40% RH2 and 60% RH3 closely matched the experimental release (FIG. 11C), providing a successful validation of this approach. In addition to fine-tuning the release of one specific protein of interest, formulations of different fusions lengths can be used to stagger the release of multiple proteins for combination therapies.

Further, the rheological properties of AcVES3 hydrogels were examined to determine whether protein encapsulation affected the shear-thin properties of the gel (FIG. 12). Four proteins (EGFP, RH1, RH3, RH5) were selected to cover the range of fusion lengths that corresponded to fast, intermediate, and slow release. All samples formed stiff hydrogels within a few minutes, with nearly identical storage moduli (~1000 Pa at 60 min). After applying a high level of strain to shear the gel, each sample rapidly recovered to its initial rigidity. These results indicate that the short fusion domains do not alter the material properties of AcVES3 and the gels retain the capability to be delivered by syringe injection.

In addition, the release of multiple proteins from the AcVES3 gel was assessed (FIGS. 13 and 14). EGFP and mRuby3 are closely related proteins, with similar net charges, that would typically exhibit the same release profile from a given peptide gel. By installing one of the longer fusion domains onto mRuby3 (RH5CmRuby3), the release of this protein from AcVES3 was slowed, whereas the unmodified EGFP was rapidly released (FIG. 13). Similar results were obtained when mRuby with or without the RH5 peptide tag was released from the AcVES3 hydrogel (FIG. 14). These result indicate that the AcVES3 peptide hydrogel could be used in conjunction with different therapeutic proteins having different peptide tags to stagger delivery of therapeutic proteins where sequential release improves treatment efficacy.

Materials and Methods

General. All reagents and kits were purchased from commercial vendors. Experiments utilizing kits or the transformation of vectors into competent cells were performed following the protocols from their respective manufacturers, which are noted below for each. LC buffers consisted of 20 mM NH4HCO3 (Std C) and 20 mM NH4HCO3 in 80% acetonitrile (Std D). HEPES buffered saline (HBS) was used for gel experiments and UV/fluorescence measurements with 1×HBS=25 mM HEPES, 150 mM NaCl, pH 7.4.

Peptide Synthesis and Purification. AcVES3 was synthesized using standard Fmoc chemistry on an ABI 433A automated peptide synthesizer, using PL-Rink resin (0.25 mmol scale). Fmoc deprotection was performed using a cocktail of 1.0% DBU, 19% piperidine in NMP and monitored to completion by conductivity. Activation of 4 eq. of amino acid was achieved with 3.6 eq. HCTU and 10 eq DIEA in NMP, and the coupling proceeded for 30 min with constant vortexing. The peptide was cleaved from resin using 95% TFA, 2.5% TIPS, and 2.5% water for 3 hr, after which the resin was filtered and the collected filtrate was concentrated. Following ether precipitation, the crude solid was dried under vacuum. AcVES3 was purified by prep-HPLC. The crude peptide was dissolved at 2 mg/mL in Std C and 5 mL per run was injected into a Waters 600 system, equipped with a Waters 2489 UV Detector and a Phenomenex PolymerX RP-1 column (250×21.2 mm, 10 µm, heated to 40° C.). A gradient of 1% Std D per min was used for 25 min, followed by 0.5% Std D per min for 150 min. The UV trace at 220 nm was monitored and fractions containing the major peptide peak were combined and lyophilized. Purity was assessed by LCMS (Shimadzu LCMS 2020) and analytical HPLC (Agilent 1200 series, PolymerX RP-1 column, 250×4.6 mm, 10 µm) using gradients of 1% Std D per min. Purified AcVES3 was converted to the sodium salt by dissolving at 1 mg/mL Std C and adding 1 eq NaOH per glutamate residue (5 eq NaOH per 1 eq peptide) using a 0.1 M NaOH stock. The solution was then frozen and lyophilized.

Plasmid Generation of EGFP Analogs. Primers (IDT) encoding genes of interest, including N-terminal cleavage sites, underwent overlapextension PCR using the Qiagen Fast Cycling PCR kit and an EGFP containing plasmid as the template. PCR products were purified using the QIAquick PCR purification kit, then subjected to Gateway BP cloning (Invitrogen) using the pDonr253 donor vector, transformed into DH5α subcloning efficiency cells (Invitrogen), and plated on LB agar plates containing 50 µg/mL spectinomycin. The plates were grown overnight at 37° C. Single colonies were picked and grown overnight in 10 mL LB media with 50 µg/mL spectinomycin at 37° C., 250 RPM. Minipreps (Qiagen) were performed to isolate amplified entry vectors. Once the sequences were validated (Macrogen), the vectors were subjected to Gateway LR cloning (Invitrogen) using the pDest527 vector, transformed into DH5α subcloning efficiency cells, and plated on LB agar plates containing 100 µg/mL ampicillin. The plates were grown overnight at 37° C. Single colonies were picked and grown overnight in 10 mL LB media with 100 µg/mL ampicillin at 37° C., 250 RPM. Minipreps were performed to isolate amplified expression vectors and the sequences were validated prior to expression. When not in use, vectors were stored at −20° C.

Expression of EGFP Analogs. Expression vectors were transformed in to Rosetta 2 DE3 pLyss competent cells (Millipore) and plated on LB Agar containing 100 µg/mL carbenecillin and 34 µg/mL chloramphenicol. The plates were grown overnight at 37° C. Single colonies were picked and grown overnight in 20 mL LB media containing 100 µg/mL carbenecillin and 34 µg/mL chloramphenicol at 37° C., 250 RPM. 5 mL of overnight culture was used to seed 500 mL of LB (100 µg/mL carbenecillin and 34 µg/mL chloramphenicol), and the culture was shaken at 37° C., 250 RPM. OD600 was monitored until reaching a value of 0.6-0.8, usually around 2-2.5 hr. At this point, the incubator temperature was reduced to 17° C. and the flasks were cooled for 15 min. To induce expression, IPTG was added to a final concentration of 0.5 mM and the flasks were shaken at 17° C., 250 RPM for 20 h. Each flask was split into 2×250 mL centrifuge bottles and spun down for 20 min at 7000 g. The supernatant was removed and the pellets were stored at −80° C. until purification.

FPLC Purification of EGFP Analogs. Pellets (from ~250 mL culture) were resuspended in 20 mL lysis buffer (50 mM sodium phosphate pH 8.0, 100 mM NaCl, 10 mM imidazole, 1× Bug Buster, and 1 EDTA-free protease inhibitor tablet) and subjected to sonication (1 amp, 1 s on, 1 s off, 1.5 min total on). The lysate was then centrifuged at 4° C., 7000 g for 20 min and the supernatant was syringe filtered (0.45 um). Using a GE P-960 sample pump, the lysate was injected into a GE ATKA FPLC system equipped with a 5 mL Talon resin column. Purification was carried out using a step gradient of 0/20/60/100% B (Buffer A: 50 mM sodium phosphate pH 8.0, 100 mM NaCl, 10 mM imidazole; Buffer B: 50 mM sodium phosphate pH 8.0, 100 mM NaCl, 100 mM imidazole). Fractions were monitored for absorbance at 280/488 nm, typically eluting at 60 and/or 100% B. Purity was confirmed by SDS PAGE gel, with the pure fractions combined and subjected to several rounds of buffer exchanges in to 50 mM sodium phosphate pH 8.0, 100 mM NaCl using Amicon Ultra-15 centrifugal filters (MWCO 10 kDa) to achieve sub-micromolar imidazole concentrations. The concentrated protein was diluted to 1.5 mL, and the concentration was determined by UV ($\varepsilon$=56000 $M^{-1}cm^{-1}$ at 488 nM). Typical yields were 20-60 mg per L culture.

FXa or TEV Protease Cleavage of EGFP Analogs. To remove the N-terminal His-6 tag encoded in the pDest527 expression vector, either FXa or TEV proteases were employed to cleave at the respective sites installed onto the fusions. For the generation of native EGFP, FXa cleavage was used to create the typical Met-containing N-terminus. The protocol followed that of the Millipore FXa cleavage/capture kit. A typical experiment would use 5 mg of NH6 (pDest527)-FXa-EGFP in 10 mL of 1× cleavage capture buffer and 100 µg of FXa (protein:enzyme weight ratio of ~50:1). The reaction was monitored by SDS PAGE gel and was typically completed within 7 hr. The reaction solution was added to prewashed p-aminobenzamidine functionalized resin to bind FXa, allowed to rock at RT for 30 min, and then the resin was filtered using an empty polypropylene column. EGFP was exchanged in to Milli-Q water using Amicon Ultra-15 filters (MWCO 10 kDa) and typically achieved near quantitative yields (~4.5 mg from 5 mg NH6 fusion). The unstructured nature of the poly-Arg containing fusions made them susceptible to non-specific cleavage by FXa, and a TEV cleavage site was installed to circumvent this. The protocol for cleavage by Halo-TEV protease (Promega) followed that of the manufacturer. A typical experiment would use 3 mg of His-6 EGFP fusion in 3 mL buffer (50 mM phosphate, pH 8.0, 100 mM NaCl), 1 mM DTT, and 10 µL HaloTEV protease. The reaction would be monitored by SDS PAGE gel and was typically completed between 3-7 hr. The completed reaction solution was added to prewashed HaloLink resin to bind HaloTEV, allowed to rock at RT for 30 min, and then the resin was filtered using an empty polypropylene column. The RH #analogs were exchanged into buffer (50 mM phosphate, pH 8.0, 100 mM NaCl) using Amicon Ultra-15 filters to reduce DTT concentration to sub-micromolar levels. Greater than 90% yields were typically achieved (~2.5 mg).

Prior to all gel experiments, the proteins were dialyzed into 2×HBS buffer (50 mM HEPES, 300 mM NaCl, pH 7.4).

UV Absorbance and Fluorescence Measurements. Protein stock concentrations in 2×HBS were determined by UV absorbance ($\varepsilon$=56000 $M^{-1}$ $cm^{-1}$ at 488 nM) using an Agilent 8453 UV-Vis spectrometer with a 1 cm cell, then diluted to a concentration of 60 µM in 2×HBS for gel experiments. All proteins exhibited typical UV spectra for EGFP, with 488/280 nm ratios of ~2.0. Baseline fluorescence spectra were obtained using a Photon Technology International Spectro-Fluorometer and a 3×3 mm cell. Samples were diluted to 30 nM to prevent detector oversaturation. All proteins exhibited similar fluorescence properties, with maxima around 507 nm and corrected fluorescence intensities of ~30,000 units.

Gel Release Experiments. AcVES3 was dissolved in cold Milli-Q water at 1 wt %. The peptide solution was vortexed for 30 s, chilled on ice for 10 min, and this process was repeated 2 more times to ensure complete dissolution of the peptide. 50 µL of peptide solution was added to a pre-chilled glass vial, followed by the addition of 50 µL pre-chilled protein (60 µM in 2×HBS)—3 vials were prepared for each protein. The vial was capped and the hydrogel was set for 1 hr at 37° C., with a final gel composition of 0.5 wt % AcVES, 30 µM protein in 1×HBS (25 mM HEPES, 150 mM NaCl, pH 7.4). After setting for 1 hr, 1 mL of 1×HBS was added to the top of the gel and the samples were incubated at 37° C. At specified time points, the supernatant was removed and replaced with 1 mL fresh 1×HBS. The UV spectrum for each supernatant was taken to determine protein concentration, which was used to quantify the number of moles per time point. The cumulatively released protein amount was compared to the initial protein loading in the gel (#mol cumulatively released protein/3.0×10$^{-9}$ mol loaded protein). Each protein supernatant was diluted to 30 nM for fluorescence measurements and the obtained spectra were normalized to that of the corresponding protein before hydrogel encapsulation.

Oscillatory Rheology. Rheological assessment was conducted on a Texas Instruments AR-G2 rheometer using a 25 mm stainless steel parallel geometry. A representative set of proteins was used to determine whether the fusion domain affected the material properties of the AcVES3 hydrogels. The 0.5 wt % gels were prepared as described in the previous section, with 150 µL of chilled AcVES3 solution mixed with 150 µL pre-chilled 2×HBS solution (with 60 µM of protein, or just buffer for empty gel). This solution was immediately applied to the center of the plate and the upper geometry was lowered to a gap height of 0.5 cm. The temperature was increased from 5° C. to 37° C. over 100 s at a constant angular frequency of 6 rad s$^{-1}$ and 0.2% strain. The storage and loss moduli were monitored for 60 min at a constant angular frequency of 6 rad s$^{-1}$ and 0.2% strain at 37° C. After the time sweep, dynamic frequency sweeps (0.1-100 rad s$^{-1}$ at constant 0.2% strain) and strain sweeps (0.1-1000% strain at constant 6 rad s$^{-1}$) were performed to ensure that time sweep data were collected in the linear viscoelastic regime. Subsequent shear thinning experiments were carried out in duplicate. Fresh samples were applied to the plate, the geometry was lowered, and the temperature was increased from 5° C. to 37° C. The moduli were monitored for 60 min (6 rad s$^{-1}$, 0.2% strain, 37° C.), followed by the application of 1000% strain for 30 s to shear the gel, after which the strain was reduced to 0.2% and the gel was allowed to recover for 60 min (6 rad s$^{-1}$, 0.2% strain).

Data Fitting and Linear Combination of EGFP Analogs. Cumulative release data was fitted to the Korsmeyer-Peppas equation:

$$\frac{M}{M_\infty} = Kt^n \quad (1)$$

where $$\frac{M}{M_\infty}$$

is the amount of protein released at time t, k is the release constant, and n is the release exponent. Excel Solver was utilized to obtain k and n of each analog by method of least squares. The predicted release was generated by summing calculated release of the analogs, scaled by the amount added as a fraction of the total concentration.

Example 3

Controlled Release of IL-7 from AcVES3 Hydrogel

This example describes use of the AcVES3 hydrogel to provide controlled release of IL-7 protein in vitro and in vivo. As discussed below, the AcVES3 hydrogel loaded with IL-7 shows superior in vitro and in vivo activity compared to soluble IL-7.

T cells are essential for the immune response to opportunistic infections, yet are deficient in subjects with HIV/AIDs, sepsis, and also in chemotherapy and bone marrow transplantation patients. Administration of IL-7 is used to maintain and increase the number and function of endogenous T cells, as well as to enhance and promote the transfer of T cells, such as in CAR T cell therapy for cancer.

For a controlled, sustained release, IL-7 was incorporated into an anionic hydrogel (AcVES3). In in vitro studies, an IL-7-dependent T cell line proliferated for greater than 18 days with a single IL-7/hydrogel insert in the culture media, comparable to a control without the IL-7/hydrogel insert where soluble IL-7 was added to the culture media every 3 days. Thus, the IL-7/AcVES3 hydrogel is significantly more efficient than soluble IL-7 for cell culture.

In in vivo murine experiments, AcVES3 hydrogel with and without 200 μg dispersed IL-7 was injected into mice, splenocytes were isolated 9 days following injection, and relevant spleen immune cell count assessed using flow cytometry. For comparison, purified IL-7 was injected at 20 μg daily or once at day 0. There were 2-3 mice in each group. The experimental protocol is depicted in FIG. 15A. As shown in FIG. 15B, a single subcutaneous injection of an IL-7/hydrogel was as effective as daily IL-7 injections, showing 2-3 fold increases in spleen T cell count.

Further, the IL-7/hydrogel greatly enhanced expansion of heterologous T cells transferred to T cell deficient mice in a model of T cell adoptive transfer (FIG. 16). CD45.1 T cells were extracted from spleens of "Pep Boy" mice and were purified using magnetic sorting. CD45.2 T cells mice were irradiated with 950 rads to ablate their lymphocytes and were subsequently injected with the CD45.1 T cells purified from the Pep Boy mice. AcVES3 hydrogels with and without IL-7 were subcutaneously injected into the flanks of the CD45.2 recipient mice and spleens and blood isolated after 7 days. As shown in FIG. 16B, there was significant expansion of $CD4^+$ and $CD8^+$ T cell populations with the IL-7/AcVES3 hydrogel relative to the hydrogel alone.

AcVES3 hydrogel biocompatibility was assessed with histology assays (FIG. 17). Cross sections of subcutaneous tissue from mice where AcVES3 hydrogel or AcVES3-IL-7 hydrogel was delivered were assessed at days 1, 11, and 30 post administration of the hydrogel. There were 9 animals in each group. On each respective day, 3 mice were euthanized, cells analyzed, and tissue H&E stained. The cross sections were analyzed by an expert veterinary pathologist. Representative images are shown in FIG. 17. As shown in FIG. 17, the AcVES3 gel alone induced a minimal (at most) lymphocytic immune response, as indicated by the low staining for neutrophils in the area of the injected gel.

In light of the above, hydrogels formed from Ac-VES3 did not elicit a lymphocytic inflammatory response when implanted in vivo, demonstrating that such hydrogels are remarkably biocompatible. In contrast, prior peptide hydrogels (e.g., formed from cationic peptides) elicit a lymphocytic response. In light of the minimal immune background of the AcVES3 hydrogel, these gels are ideal materials for delivery of therapeutic proteins (such as cytokines, for example, IL-7) that modulate lymphocytic behavior.

It will be apparent that the precise details of the methods or compositions described may be varied or modified without departing from the spirit of the described embodiments. We claim all such modifications and variations that fall within the scope and spirit of the claims below.

It is claimed:

1. An isolated peptide, comprising or consisting of an amino acid sequence set forth as one of:

(1)
XBXSXSXBX$^D$PPXBXSXBXBX;

(2)
XBXSXSXBX$^D$PGXBXSXBXBX;
or (3)
(SEQ ID NO: 2)
XBXSXSXBX NGXBXSXBXBX wherein each X is independently selected from any one of L, I, T, and V;

each B is independently selected from any one of D, E, and S;

the $^D$P is a proline that is a D amino acid;

the C-terminus of the peptide is amidated or free carboxylic acid;

the N-terminus of the peptide is acetylated or free amine; and the peptide is no more than 50 amino acids in length.

2. The isolated peptide of claim 1, comprising or consisting of an amino acid sequence set forth as one of:

(1a)
XEXSXSXEX$^D$PPXEXSXEXEX;

(2a)
XEXSXSXEX$^D$PGXEXSXEXEX;
or (3a)
(SEQ ID NO: 3)
XEXSXSXEX NGXEXSXEXEX.

3. The isolated peptide of claim 1, comprising an amino acid sequence set forth as one of:

(1b)
VEVSVSVEV$^D$PPTEVSVEVEV;

(2b)
VEVSVSVEV$^D$PGTEVSVEVEV;
or (3b)
(SEQ ID NO: 4)
VEVSVSVEV NGTEVSVEVEV.

4. The isolated peptide of claim 3, consisting of the AcVES3 peptide:

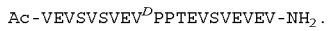Ac-VEVSVSVEV$^D$PPTEVSVEVEV-NH$_2$.

5. The isolated peptide of claim 1, wherein the C-terminus of the peptide is amidated and the N-terminus of the peptide is acetylated.

6. The isolated peptide of claim 1, wherein the peptide forms an amphiphilic β-hairpin conformation in an aqueous solution comprising 150 mM NaCl and a pH of 7.4 at 25-37° C.

7. The isolated peptide of claim 1, wherein:
an aqueous solution containing 2% w/v of the peptide and 150 mM NaCl and a pH of 7.4 forms a peptide hydrogel comprising a fibrillar network of a plurality of the peptide when incubated at 25-37° C. in a container; and
the hydrogel undergoes a gel-sol phase transition upon application of shear stress, and a sol-gel phase transition upon removal of the shear stress.

8. The isolated peptide of claim 1, wherein the peptide is from 20 to 50 amino acids in length.

9. A peptide hydrogel formed with the isolated peptide of claim 1.

10. The peptide hydrogel of claim 9, further comprising at least one heterologous protein dispersed within the peptide hydrogel.

11. The peptide hydrogel of claim 10, wherein the heterologous protein is a therapeutic protein.

12. The peptide hydrogel of claim 11, wherein the therapeutic protein is a cytokine.

13. The peptide hydrogel of claim 10, wherein the heterologous protein is one of IL-7, IL-2, IL-15, or a heterodimer of IL-15 and IL-15Rα.

14. The peptide hydrogel of claim 10, wherein the heterologous protein is fused to a peptide tag having a net positive charge that increases retention of the heterologous protein in the hydrogel.

15. The peptide hydrogel of claim 10, wherein the heterologous protein is fused to a peptide tag having a net negative charge that decreases retention of the heterologous protein in the hydrogel.

16. A syringe, containing the peptide hydrogel of claim 10.

17. A method of administrating a heterologous protein to a subject, comprising administering the peptide hydrogel of claim 10 to the subject.

18. The isolated peptide of claim 1, fused to an integrin binding peptide.

19. The isolated peptide of claim 18, wherein the isolated peptide is fused to the integrin binding peptide by a heterologous peptide linker.

20. The isolated peptide of claim 18, wherein the amino acid sequence of the integrin binding peptide is set forth as any one of RGDV (SEQ ID NO: 5), KQAGDV (SEQ ID NO: 6), RLD, KRLDGS (SEQ ID NO: 7), LDV, IDS, LET, IET, YYDLR (SEQ ID NO: 8), or FYFDLR (SEQ ID NO: 9).

21. The isolated peptide of claim 20, wherein the amino acid sequence of the integrin binding peptide is set forth as RGDV (SEQ ID NO: 5).

22. The isolated peptide of claim 18, wherein the isolated peptide fused to the integrin binding peptide comprises the amino acid sequence set forth as:

YEVSVSYEV$^D$PPTEVSYEYEVGGGGRGDV.

23. The isolated peptide of claim 22, wherein the isolated peptide fused to the integrin binding peptide consists of the AcVES3-RGDV peptide:

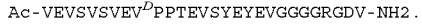Ac-VEVSVSVEV$^D$PPTEVSYEYEVGGGGRGDV-NH2.

24. A peptide hydrogel formed with the isolated peptide of claim 18.

25. The peptide hydrogel of claim 24, further comprising:
mammalian cells dispersed within the peptide hydrogel, wherein the mammalian cells comprise a cell surface comprising one or more integrin proteins that bind to the integrin binding peptide.

26. The peptide hydrogel of claim 25, wherein the mammalian cells express a therapeutic protein.

27. The peptide hydrogel of claim 25, wherein the mammalian cells are chimeric antigen receptor (CAR) T cells.

28. The peptide hydrogel of claim 25, wherein binding of the integrin binding peptide to the one or more integrin proteins increases retention of the mammalian cells in the peptide hydrogel.

29. A syringe, containing the peptide hydrogel of claim 25.

30. A method of administrating a heterologous cell to a subject, comprising administering the peptide hydrogel of claim 25 to the subject.

31. A method of culturing mammalian cells in a three-dimensional matrix, comprising:
mixing the peptide of claim 18 and mammalian cells under conditions sufficient to form a peptide hydrogel encapsulating the mammalian cells, wherein the mammalian cells comprise a cell surface comprising one or more integrin proteins that bind to the integrin binding peptide fused to the AcVES3 peptide; and
incubating the mammalian cells under conditions sufficient for cell growth and proliferation.

32. The peptide hydrogel of claim 9, wherein the hydrogel undergoes a gel-sol phase transition upon application of shear stress, and a sol-gel phase transition upon removal of the shear stress;
the hydrogel comprises a storage modulus of greater than 40 Pascal in the absence of shear;
the hydrogel comprises from about 10 mM to about 400 mM NaCl and a pH of from about 7.0 to about 9.0;
the hydrogel comprises from about 0.25% to about 4.0% w/v peptide; and/or
the hydrogel does not induce a lymphocytic immune response when administered to a subject.

* * * * *